US009709468B2

(12) United States Patent
Ebi et al.

(10) Patent No.: US 9,709,468 B2
(45) Date of Patent: Jul. 18, 2017

(54) SAMPLE PREPARATION DEVICE, CELL ANALYZER, AND FILTER MEMBER

(71) Applicant: Sysmex Corporation, Kobe-shi, Hyogo (JP)

(72) Inventors: Ryuichiro Ebi, Kobe (JP); Koki Tajima, Kobe (JP); Toshikuni Suganuma, Kobe (JP)

(73) Assignee: SYSMEX CORPORATION, Kobe-Shi, Hyogo (JP)

( * ) Notice: Subject to any disclaimer, the term of this patent is extended or adjusted under 35 U.S.C. 154(b) by 0 days.

(21) Appl. No.: 14/671,501

(22) Filed: Mar. 27, 2015

(65) Prior Publication Data

US 2015/0198508 A1   Jul. 16, 2015

Related U.S. Application Data

(63) Continuation of application No. PCT/JP2013/076053, filed on Sep. 26, 2013.

(30) Foreign Application Priority Data

Sep. 28, 2012 (JP) ................................ 2012-217631

(51) Int. Cl.
*G01N 33/00* (2006.01)
*G01N 21/75* (2006.01)
(Continued)

(52) U.S. Cl.
CPC ............ *G01N 1/28* (2013.01); *C12N 5/0682* (2013.01); *G01N 1/4077* (2013.01);
(Continued)

(58) Field of Classification Search
USPC .......... 422/527, 422, 513, 534, 73; 210/645, 210/808, 90, 97, 137
See application file for complete search history.

(56) References Cited

U.S. PATENT DOCUMENTS

| 5,578,459 A | 11/1996 | Gordon et al. |
| 5,976,824 A | 11/1999 | Gordon |

(Continued)

FOREIGN PATENT DOCUMENTS

| CN | 102033012 A | 4/2011 |
| CN | 102105226 A | 6/2011 |

(Continued)

OTHER PUBLICATIONS

Copy of International Preliminary Report on Patentability with English translation for PCT/JP2013/076053 dated Apr. 9, 2015, 18 pages.

*Primary Examiner* — Dean Kwak
(74) *Attorney, Agent, or Firm* — Brinks Gilson & Lione

(57) ABSTRACT

A sample preparation device includes: a filter member including a filter configured to separate cells being an analysis target from other components in a sample; a first receptacle and a second receptacle configured to be connected to each other via the filter; a third receptacle capable of holding the sample therein; a negative pressure section configured to apply a negative pressure into the second receptacle, thereby to move the sample in the third receptacle toward the filter via the first receptacle, and thereby to move components other than the analysis target into the second receptacle via the filter; and a positive pressure section configured to apply a positive pressure from the second receptacle side to the filter to which cells being the analysis target are attached.

24 Claims, 19 Drawing Sheets

(51) Int. Cl.
*B01L 3/02* (2006.01)
*B01D 35/00* (2006.01)
*G01N 1/28* (2006.01)
*G01N 1/40* (2006.01)
*C12N 5/071* (2010.01)
*G01N 33/487* (2006.01)
*G01N 15/10* (2006.01)
*G01N 15/14* (2006.01)

(52) U.S. Cl.
CPC ..... *G01N 33/4875* (2013.01); *G01N 15/1459* (2013.01); *G01N 2001/4088* (2013.01); *G01N 2015/1006* (2013.01)

(56) References Cited

U.S. PATENT DOCUMENTS

| | | |
|---|---|---|
| 2006/0060531 A1 | 3/2006 | Coville et al. |
| 2008/0108103 A1 | 5/2008 | Ishisaka et al. |
| 2010/0291588 A1* | 11/2010 | McDevitt .......... B01L 3/502715 435/7.2 |
| 2011/0076755 A1* | 3/2011 | Ebi .................... B01F 13/0818 435/287.3 |
| 2011/0176934 A1 | 7/2011 | Ebi et al. |
| 2011/0315641 A1 | 12/2011 | Curran et al. |

FOREIGN PATENT DOCUMENTS

| | | |
|---|---|---|
| CN | 102183451 A | 9/2011 |
| EP | 2 306 171 A2 | 4/2011 |
| EP | 2 345 885 A2 | 7/2011 |
| JP | 2011-095247 A | 5/2011 |
| JP | 2011-164081 A | 8/2011 |
| JP | 2012-139112 A | 7/2012 |
| WO | WO 95/14533 A1 | 6/1995 |
| WO | WO 98/20352 A2 | 5/1998 |
| WO | WO 2006/103920 A1 | 10/2006 |
| WO | WO 2010/010355 A2 | 1/2010 |
| WO | WO 2011/078784 A1 | 6/2011 |

* cited by examiner

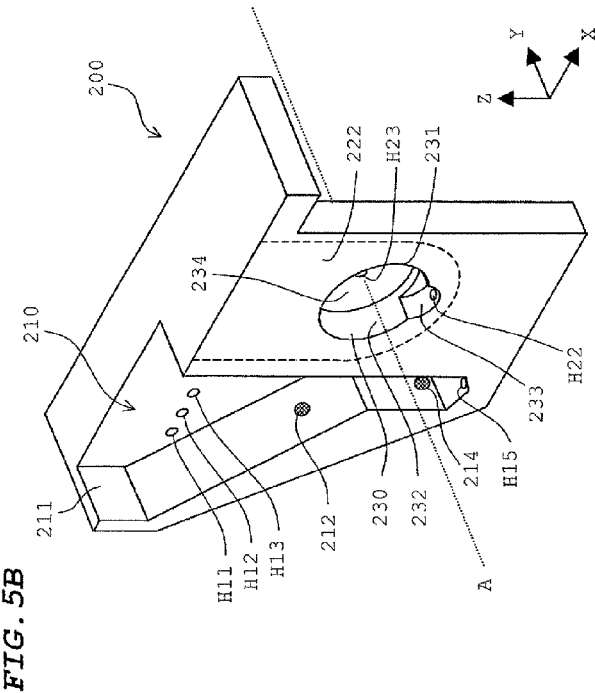
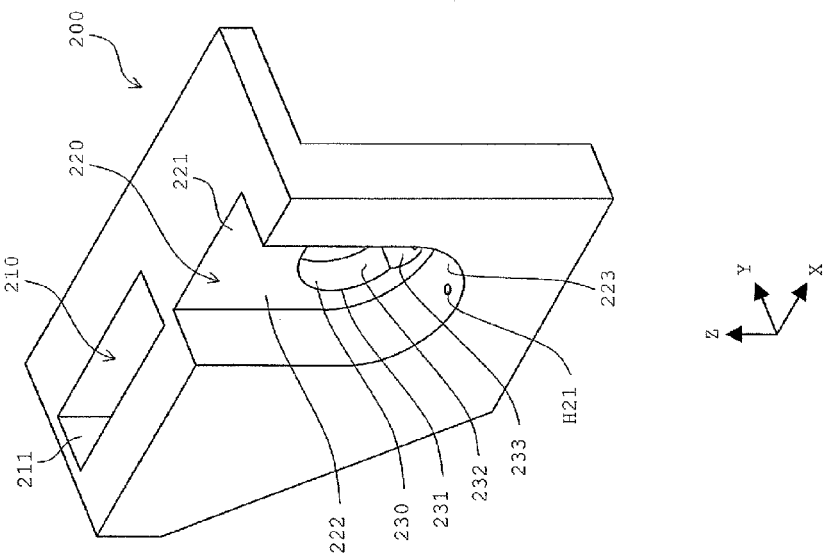
FIG. 5A
FIG. 5B
FIG. 5C

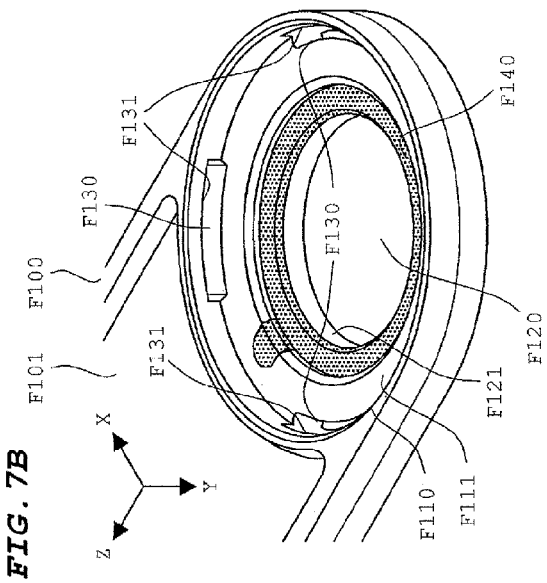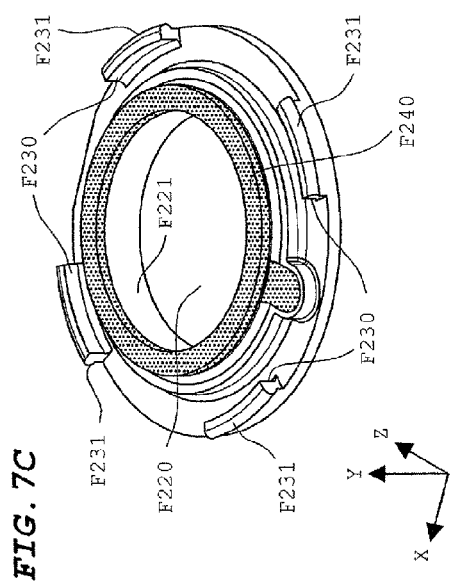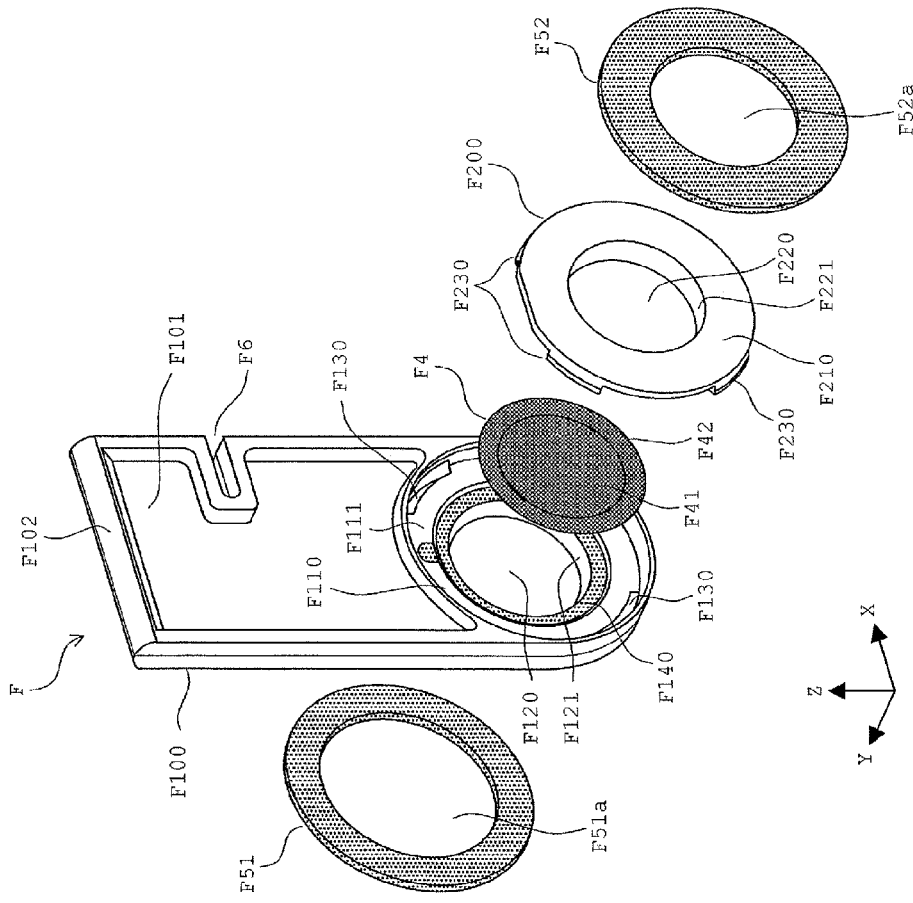

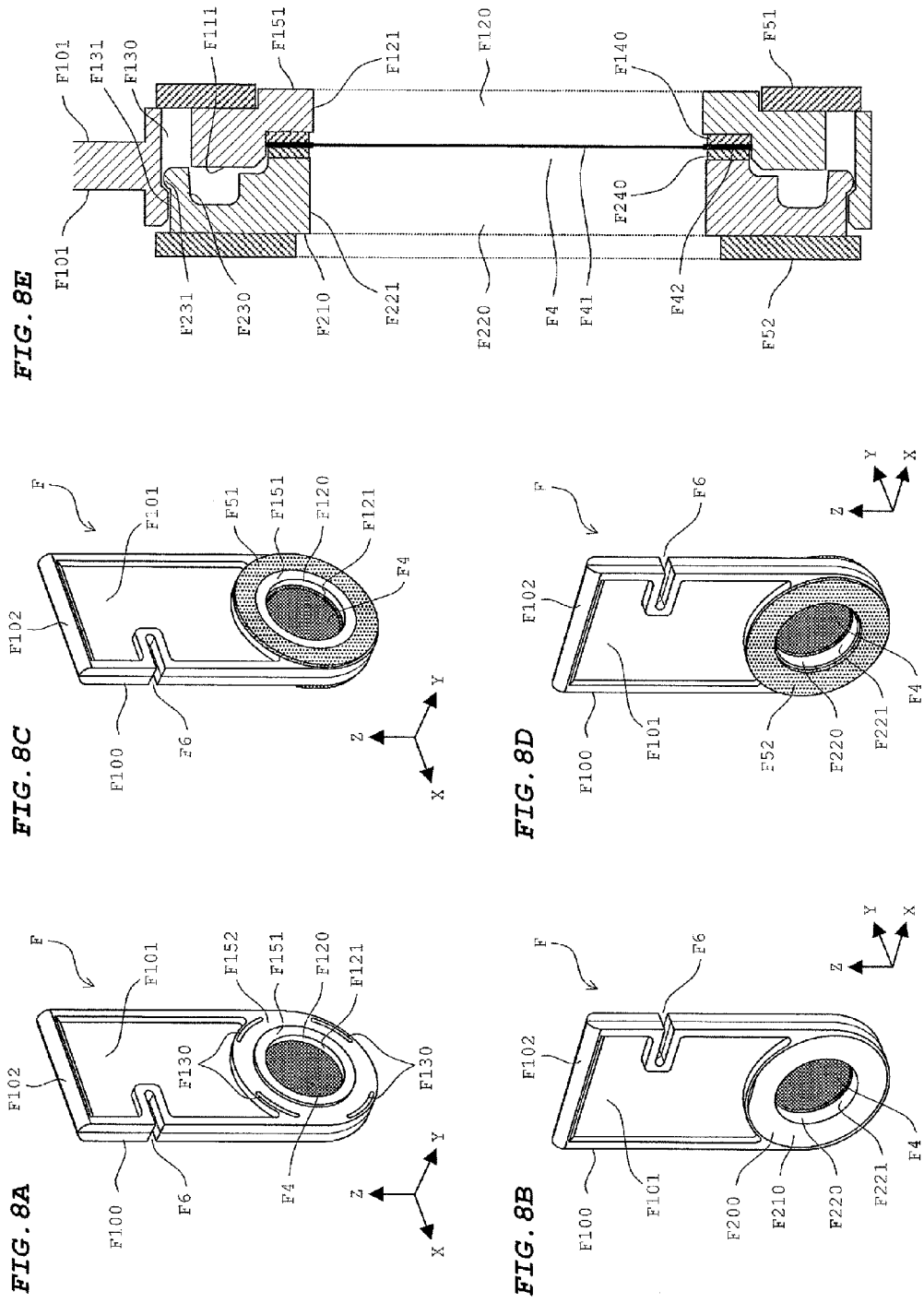

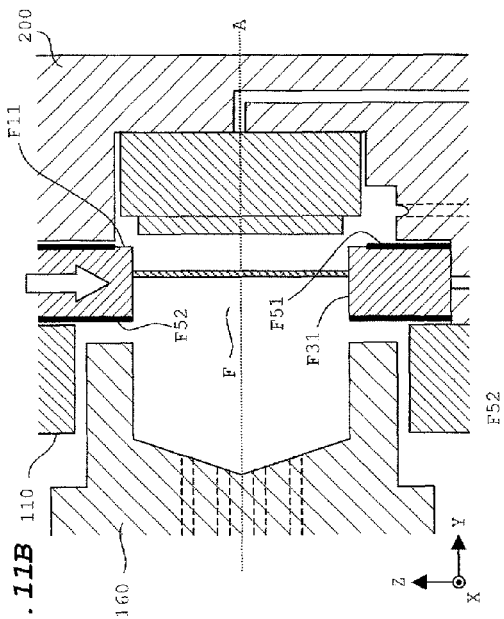
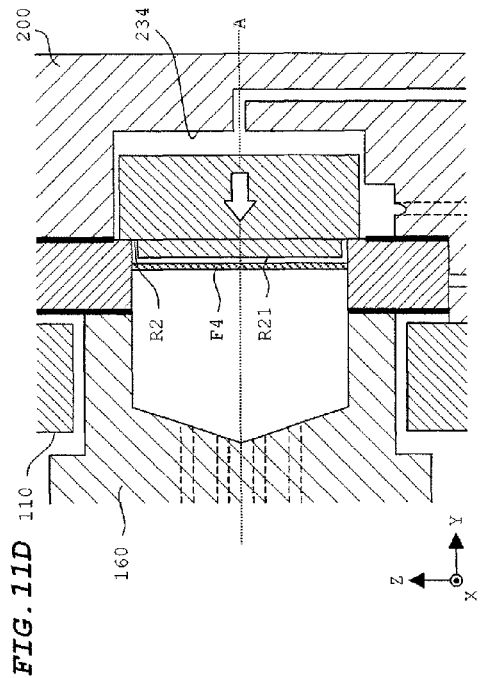
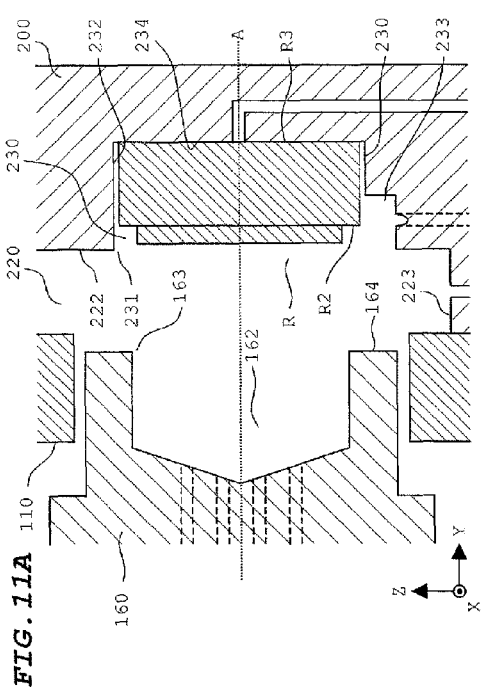
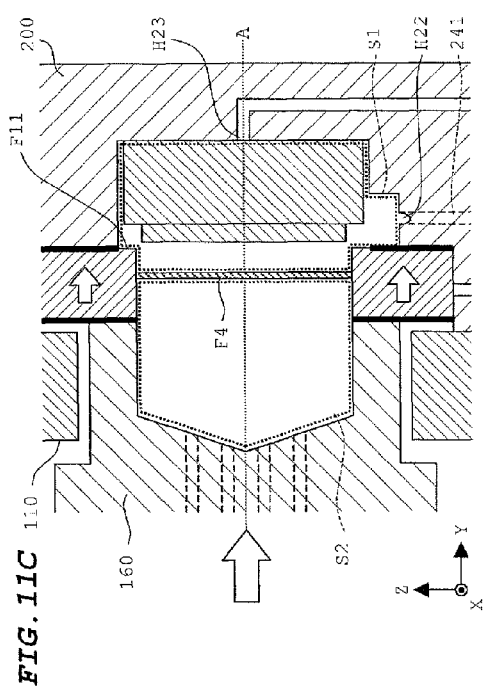

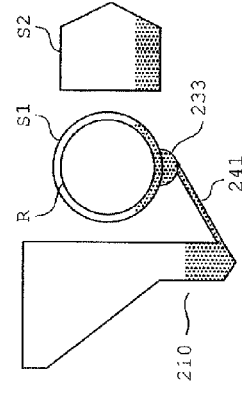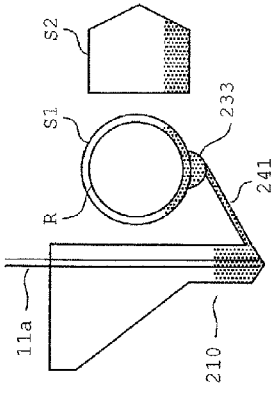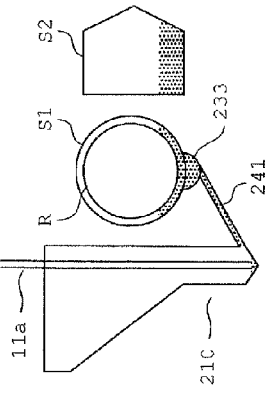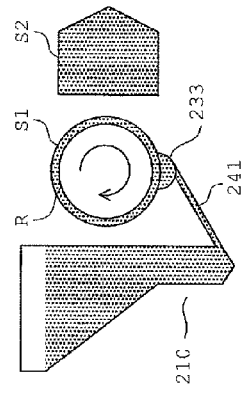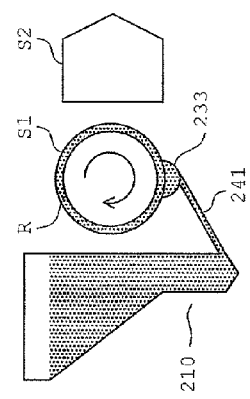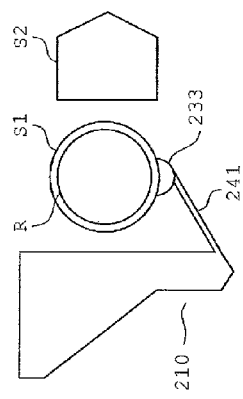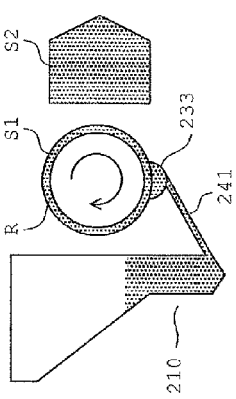

SAMPLE PREPARATION DEVICE, CELL ANALYZER, AND FILTER MEMBER

CROSS REFERENCE TO RELATED APPLICATIONS

This application is a continuation of International Application No. PCT/JP2013/076053 filed on Sep. 26, 2013, entitled "SAMPLE PREPARATION DEVICE, CELL ANALYZER, AND FILTER MEMBER", which claims priority under 35 U.S.C. Section 119 of Japanese Patent Application No. 2012-217631 filed on Sep. 28, 2012, entitled "SAMPLE PREPARATION DEVICE AND CELL ANALYZER". The disclosure of the above applications is incorporated herein by reference.

BACKGROUND OF THE INVENTION

1. Field of the Invention

The present invention relates to a sample preparation device which prepares a measurement sample from cells collected from a subject, a cell analyzer which analyzes the prepared sample, and a filter member for preparing the measurement sample.

2. Disclosure of Related Art

To date, there have been known cell analyzers which analyze cells contained in a biological sample collected from a living body. For example, there is known a cell analyzer which measures, by use of a flow cytometer, epidermal cells contained in a sample collected from the uterine cervix of a subject and which determines the state of advancement of canceration based on the result of the measurement.

Such a cell analyzer analyzes individual cells. Thus, in order to increase the accuracy of the analysis, it is desirable that the number of cells being an analysis target is larger. For example, there is known a sample preparation device that can increase the concentration of cells contained in the sample, thereby being able to increase the number of cells being the analysis target while suppressing the amount of the sample.

This sample preparation device includes: a storage chamber whose upper face is open and which stores a sample therein; a cylindrical piston which is inserted in this storage chamber and whose lower end face has a filter mounted thereto; an aspiration tube which aspirates a liquid that has entered the piston through the filter; and a stirrer disposed in a bottom portion of the storage chamber. In a step of concentrating a sample, first, the sample is put into the storage chamber, and then, the piston is inserted into the storage chamber until the filter is immersed in the sample. At this time, liquid that has leaked into the piston is aspirated by the aspiration tube, to be removed from the storage chamber. Cells being the analysis target do not pass through the filter and attach to the lower face of the filter. The cells attached to the lower face of the filter are removed from the filter, by the stirrer being driven as appropriate. As a result, the sample having an increased concentration of cells being the analysis target remains in the storage chamber.

However, in this sample preparation device, liquid that has leaked into the piston in association with insertion of the piston into the storage chamber is discharged by use of the aspiration tube. Thus, it is difficult to completely aspirate the liquid in the storage chamber. This may cause a large amount of cells other than cells being the analysis target to remain in the storage chamber. In addition, with this sample preparation device, in order to perform the process of concentrating cells being the analysis target, the piston needs to be moved up and down many times in the storage chamber. Thus, the concentrating process may take time.

SUMMARY OF THE INVENTION

A first aspect of the present invention relates to a sample preparation device. The sample preparation device according to this aspect includes: a filter member including a filter configured to separate cells being an analysis target from other components in a sample; a first receptacle and a second receptacle configured to be connected to each other via the filter; a third receptacle capable of holding the sample therein; a communication hole formed in the first receptacle and configured to allow the sample to go into and out of the first receptacle; a flow path configured to allow the third receptacle to be communicated with the communication hole; a negative pressure section configured to apply a negative pressure into the second receptacle, thereby to move the sample in the third receptacle toward the filter via the flow path and the first receptacle, and thereby to move components other than the analysis target into the second receptacle via the filter; and a positive pressure section configured to apply a positive pressure from the second receptacle side to the filter to which cells being the analysis target are attached.

The sample preparation device according to this aspect includes a configuration that moves the sample in the first receptacle through the filter into the second receptacle by use of a negative pressure. Therefore, the liquid present in the first receptacle can be completely aspirated to the second receptacle side, and the amount of components other than the analysis target remaining in the first receptacle can be reduced as much as possible. In addition, in this sample preparation device, the process of concentrating cells being the analysis target can be performed by use of a negative pressure and a positive pressure without moving the filter, and thus, the concentrating process can be performed quickly. Accordingly, it is possible to increase efficiency in generating the sample in which cells being the analysis target are concentrated.

A second aspect of the present invention relates to a cell analyzer. The cell analyzer according to this aspect includes: the sample preparation device according to the first aspect; and an analysis section configured to analyze cells contained in a measurement sample prepared by the sample preparation device.

With the cell analyzer according to this aspect, effects similar to those in the first aspect can be obtained. Since the efficiency in generating the sample is increased, a larger amount of the concentrated sample can be collected, and a larger amount of the sample can be subjected to the analysis. Accordingly, the accuracy of analysis can be increased.

A third aspect of the present invention relates to a filter member. The filter member according to this aspect includes: a filter configured to separate cells being an analysis target from other components in a sample; a filter holding member including a through-hole having a first opening and a second opening; and an elastic body located at a distance from a boundary of the first opening. The filter is located at a position displaced inwardly from an edge of a cylindrical portion formed by the through-hole.

With the filter member according to this aspect, it is possible to improve the liquid tightness between the filter member and the receptacle located to the first opening side, by means of the elastic body. Since the elastic body is located so as to be distanced from the boundary of the first opening, it is possible to avoid contact between the elastic body and the rotating member for removing cells attached to the filter. Thus, drive of the rotating member can be smoothly performed. In addition, since the filter is located at a position displaced inwardly from the edge of the cylindrical portion, the rotating member for removing cells attached to the filter can be driven while being brought close to the filter.

BRIEF DESCRIPTION OF THE DRAWINGS

The above and other objects and new features of the present invention will be fully clarified by the following description of the embodiment, when read in conjunction with accompanying drawings.

FIGS. 5A to 5C are respectively a perspective view showing a configuration of a receptacle body, a perspective view of the receptacle body when cut, and a side view of the receptacle body, according to the embodiment;

FIGS. 7A to 7C show a detailed configuration of the filter member according to the embodiment;

FIGS. 8A to 8E show a detailed configuration of the filter member according to the embodiment;

FIGS. 11A to 11D illustrate a procedure of setting the filter member according to the embodiment;

FIGS. 16A to 16I are schematic diagrams showing states of liquids in the receptacles and spaces according to the embodiment;

Figure 1:
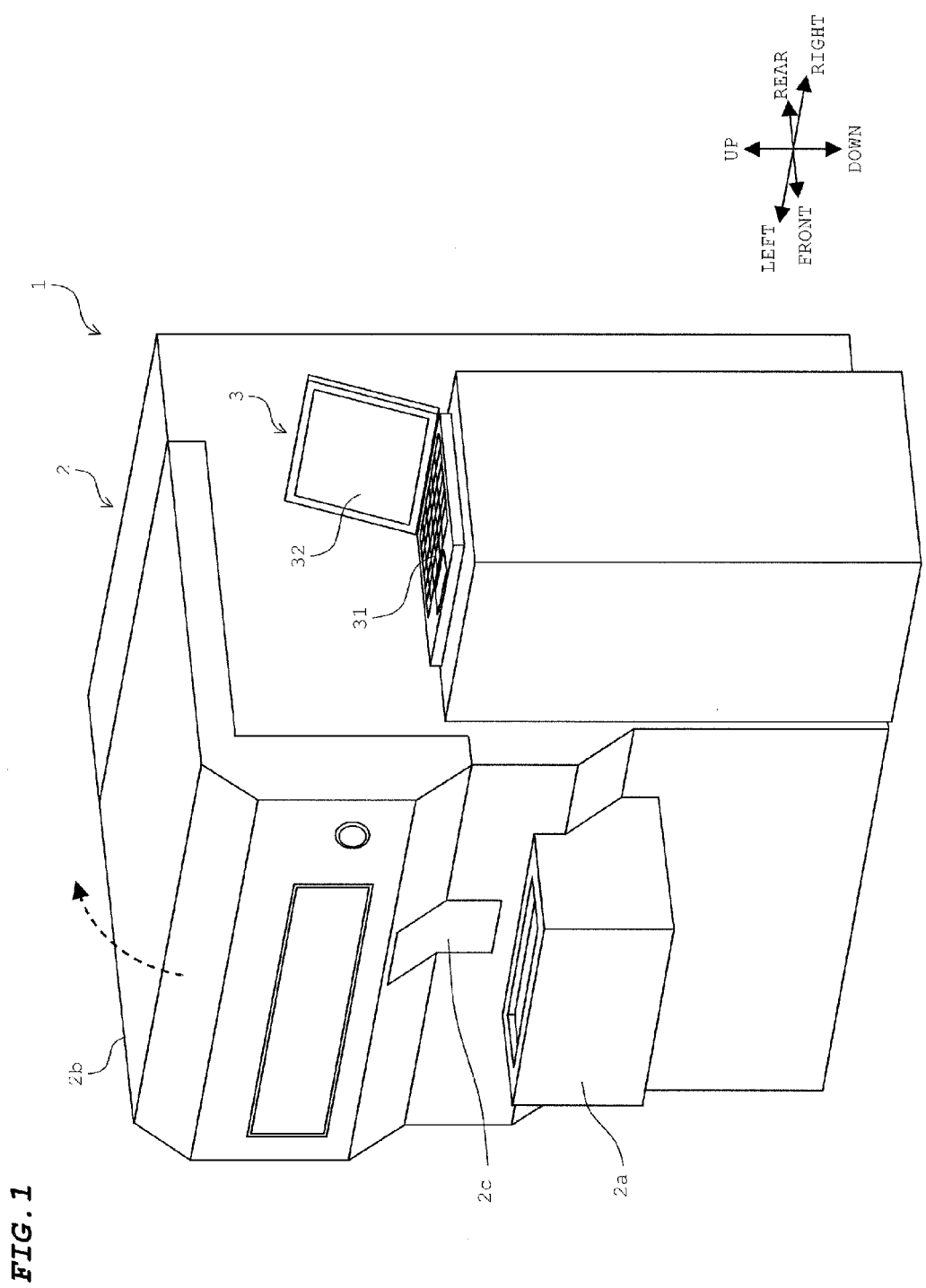
FIG. 1 is a perspective view showing an external configuration of a canceration information providing apparatus according to an embodiment.

It should be noted that the drawings are solely for description and do not limit the scope of the present invention by any degree.

DESCRIPTION OF PREFERRED EMBODIMENTS

The present embodiment is realized by applying the present invention to a canceration information providing apparatus (cell analyzer) that prepares a measurement sample which contains cells (biological sample) collected from a subject (patient), the canceration information providing apparatus obtaining information regarding canceration of cells based on the prepared measurement sample. Hereinafter, a canceration information providing apparatus 1 according to the present embodiment will be described with reference to the drawings.

In the present embodiment, a canceration information providing apparatus 1 corresponds to "cell analyzer" described in claims. A measurement apparatus 2 corresponds to "analysis section" described in claims. A data processing apparatus 3 corresponds to "display section" and "analysis section" described in claims. A separation/substitution section 14 corresponds to "sample preparation device" described in claims. A preparation control section 28 corresponds to "display section" described in claims. A hole 120b corresponds to "insertion hole" described in claims. A sensor 122 corresponds to "light source" and "light receiver" described in claims. A piston 160 corresponds to "pressing mechanism" described in claims. A recess 162 corresponds to "second receptacle" described in claims. A receptacle 210 corresponds to "third receptacle" described in claims. A recess 230 corresponds to "first receptacle" described in claims. A pneumatic source 294 corresponds to "negative pressure section" and "positive pressure section" described in claims. A face F11 corresponds to "abutment portion" described in claims. A hole F3 corresponds to "cylindrical portion" and "through-hole" described in claims. Rubbers F51 and F52 correspond to "elastic body" described in claims. A bar code label F8 corresponds to "identification body" described in claims. A RFID tag F9 corresponds to "identification body" described in claims. An upper end portion F102 corresponds to "deformed portion" described in claims. A ridge portion F103 corresponds to "deformed portion" described in claims. A hole F120 corresponds to "cylindrical portion" and "through-hole" described in claims. A face F151 corresponds to "abutment portion" described in claims. A hole F220 corresponds to "cylindrical portion" and "through-hole" described in claims. A hole H22 corresponds to "communication hole" described in claims. A hole H23 corresponds to "liquid supply part" and "substitution liquid inlet" described in claims. A hole H32 corresponds to "vent hole" described in claims. A negative pressure source P11 corresponds to "negative pressure section" described in claims. A positive pressure source P12 corresponds to "positive pressure section" described in claims. A regulator P13 corresponds to "negative pressure section" described in claims. A stirrer R corresponds to "rotating member" described in claims. A face R2 corresponds to "restraining portion" described in claims. A protrusion R21 corresponds to "inner circular portion" described in claims. However, the correspondence between the claims and the present embodiment is merely an example, and does not limit the claims to the present embodiment.

FIG. 1 is a perspective view showing an external configuration of the canceration information providing apparatus 1.

The canceration information providing apparatus 1 flows, into a flow cell, a measurement sample containing cells (hereinafter, referred to as "analysis target cells") collected from a subject, and emits a laser beam to the measurement sample flowing in the flow cell. Then, the canceration information providing apparatus 1 detects lights (forward scattered light, side scattered light, and side fluorescence) from the measurement sample and analyzes light signals thereof, to determine whether the cells include cells that are cancerous or becoming cancerous. Specifically, in a case where cervical cancer is to be screened by use of epidermal cells of the uterine cervix collected from a subject, the canceration information providing apparatus 1 is used.

The canceration information providing apparatus 1 includes: a measurement apparatus 2 which performs measurement and the like of analysis target cells; and a data processing apparatus 3 which is connected to the measurement apparatus 2 and performs analysis and the like of measurement results. To the front face of the measurement apparatus 2, a specimen setting section 2a is provided in which to set a plurality of sample containers 4 (see FIG. 2) each containing a mixed liquid (sample) composed of cells collected from the uterine cervix of a subject and a preservative liquid whose major component is methanol. The measurement apparatus 2 is provided with a cover 2b, and a user can access the inside of the measurement apparatus 2 by opening the cover 2b upwardly. The measurement apparatus 2 is also provided with an opening 2c for allowing a specimen pipette section 11 described later to come out of and go into the measurement apparatus 2. The data processing apparatus 3 includes an input section 31 which receives instructions from the user, and a display section 32 which displays analysis results and the like.

Figure 2:
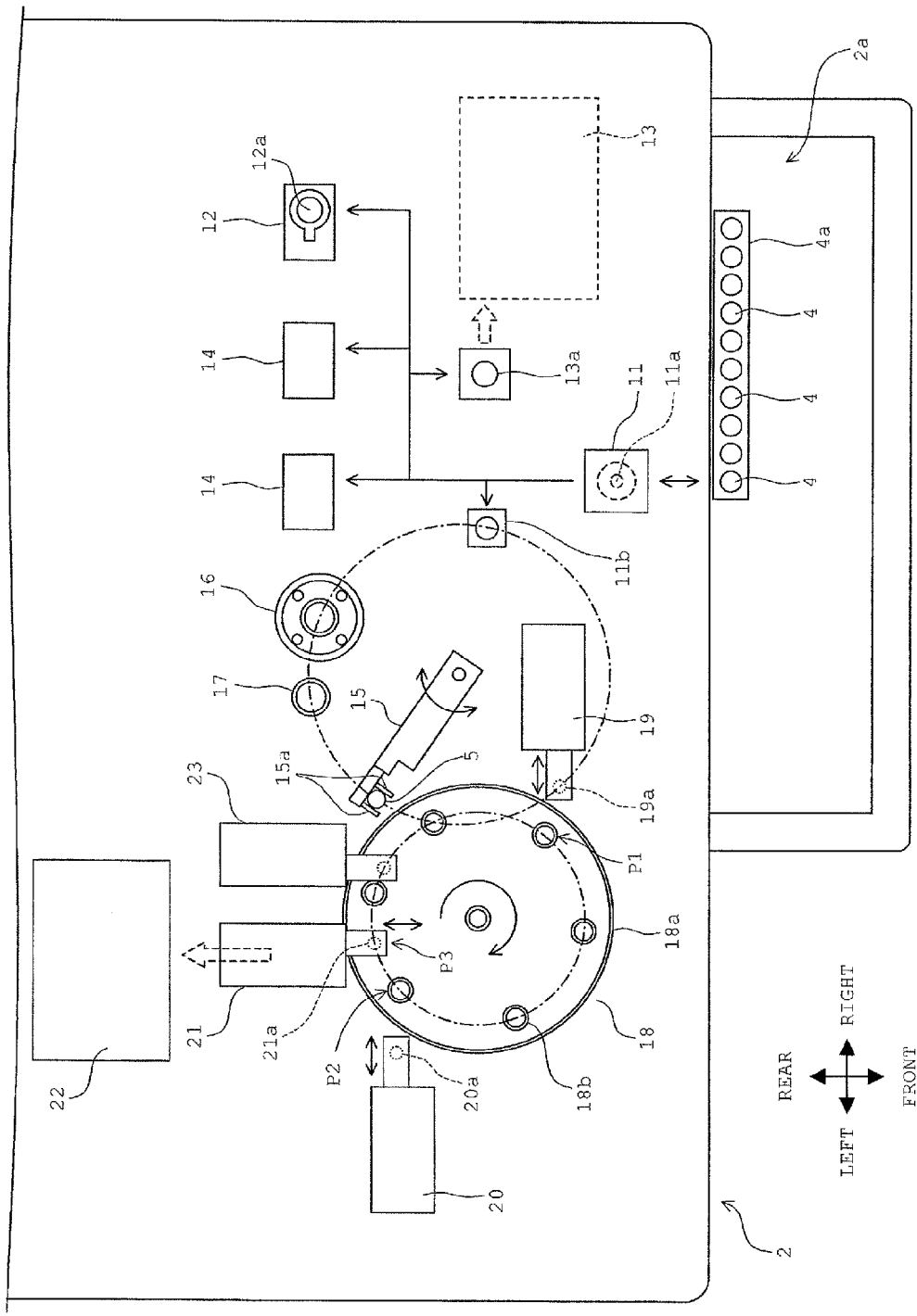
FIG. 2 is a plan view showing a configuration of the inside of a measurement apparatus according to the embodiment.

FIG. 2 is a plan view showing a configuration of the inside of the measurement apparatus 2.

The specimen setting section 2a sequentially transports a rack 4a on which a plurality of sample containers 4 are set, to a sample aspiration position for the specimen pipette section 11. The specimen pipette section 11 includes a pipette 11a extending in the vertical direction, and is configured to move the pipette 11a in the horizontal direction and the vertical direction, thereby to be able to aspirate and discharge a sample.

When a sample container 4 is located at the aspiration position in the specimen setting section 2a, the sample contained in this sample container 4 is aspirated by the specimen pipette section 11, to be discharged into a sample receptacle 12a of a first dispersion section 12. By applying a shearing force, the first dispersion section 12 disperses aggregated cells contained in the sample. The sample for which the process (first dispersion process) has been completed by the first dispersion section 12 is aspirated by the specimen pipette section 11, to be discharged into a sample taking-in section 13a of a secondary detection section 13. The secondary detection section 13 includes a flow cytometer, and measures the concentration of the sample by detecting (pre-measurement) the number of analysis target cells. Based on this concentration measurement, an aspiration amount of the sample necessary for a primary detection section 22 to perform primary measurement is determined.

Next, the sample held in the sample receptacle 12a of the first dispersion section 12 is aspirated by the specimen pipette section 11 by the aspiration amount as determined above, and the aspirated sample is discharged into a receptacle 210 (see FIG. 5A) of a separation/substitution section 14. Two separation/substitution sections 14 are provided so as to perform the process in parallel.

The separation/substitution section 14 substitutes, with a diluent, the preservative liquid whose major component is methanol and which is included in the sample. That is, the separation/substitution section 14 performs a process of diluting, with the diluent, the concentration of methanol included in the sample, such that a cell staining process being a post-step can be appropriately performed. As the diluent, Tris-HCl (tris buffer) is used. In addition, the separation/substitution section 14 separates analysis target cells (epidermal cells of the uterine cervix) contained in the sample from the other cells (red blood cells, white blood cells, bacteria, and the like) and contaminants. Accordingly, a concentrate is obtained in which analysis target cells are concentrated so as to include cells by a number necessary for detecting cancerous cells. A detailed configuration of the separation/substitution section 14 will be described later.

Next, a measurement sample container 5 set in a holder 18b of a reaction section 18 is gripped by a pincers-like gripper 15a of a container transfer section 15, to be located at sample loading section 11b. Subsequently, the concentrate held in the receptacle 210 of the separation/substitution section 14 is aspirated by the specimen pipette section 11, to be discharged into a measurement sample container 5 located at the sample loading section 11b. The container transfer section 15 transfers this measurement sample container 5 to a second dispersion section 16.

The second dispersion section 16 applies ultrasonic vibration to the sample concentrated in the separation/substitution section 14. Accordingly, aggregated cells remaining after the first dispersion process are dispersed into single cells. The measurement sample container 5 for which the process (second dispersion process) by the second dispersion section 16 has been completed is set in a liquid removing section 17 by the container transfer section 15. The liquid removing section 17 removes (dries out) liquid attached to the external surface of the measurement sample container 5. The measurement sample container 5 for which the process by the liquid removing section 17 has been completed is set in a holder 18b of the reaction section 18 by the container transfer section 15.

The reaction section 18 heats the measurement sample container 5 set in the holder 18b to a predetermined temperature (about 37 degrees), to accelerate the reaction between the sample in the measurement sample container 5 and reagents added by a first reagent adding section 19 and a second reagent adding section 20. In addition, the reaction section 18 includes a round turn table 18a configured to be rotatable. In an outer periphery portion of the turn table 18a, a plurality of holders 18b are provided such that measurement sample containers 5 can be set therein.

The first reagent adding section 19 and the second reagent adding section 20 respectively include supply parts 19a and 20a movable to positions P1 and P2 above measurement sample containers 5 set in the turn table 18a. The first reagent adding section 19 and the second reagent adding section 20 respectively add predetermined amounts of reagents from the supply parts 19a and 20a into a measurement sample container 5 when the measurement sample container 5 has been transported to the position P1, P2 by the turn table 18a.

The reagent to be added by the first reagent adding section 19 is a RNase for performing an RNA removing process on cells, and the reagent to be added by the second reagent adding section 20 is a staining liquid for performing a DNA staining process on cells. Through the RNA removing process, RNA is degraded in each cell, which makes it possible to measure only DNA in the cell nucleus. The DNA staining process is performed by means of propidium iodide (P1) which is a fluorescent staining liquid that contains a dye. Through the DNA staining process, the nucleus in each cell is selectively stained. Accordingly, it becomes possible to detect fluorescence from the nucleus.

A sample aspiration section 21 includes a pipette 21a movable to a position P3 above a measurement sample container 5 set in the turn table 18a, and aspirates the measurement sample in a measurement sample container 5 when the measurement sample container 5 has been transported to the position P3 by the turn table 18a. The sample aspiration section 21 is connected to a flow cell of the primary detection section 22, via a flow path not shown, and supplies the measurement sample aspirated by the pipette 21a to the flow cell of the primary detection section 22.

The primary detection section 22 includes a flow cytometer for detecting lights (forward scattered light, side scattered light, and side fluorescence) from the measurement sample, and outputs signals based on the respective lights, to a circuit in a later stage. A container cleaning section 23 discharges a cleaning liquid into a measurement sample container 5 set in the turn table 18a, thereby to clean the inside of the measurement sample container 5 after the measurement sample thereof has been supplied to the sample aspiration section 21 to the primary detection section 22.

Figure 3:
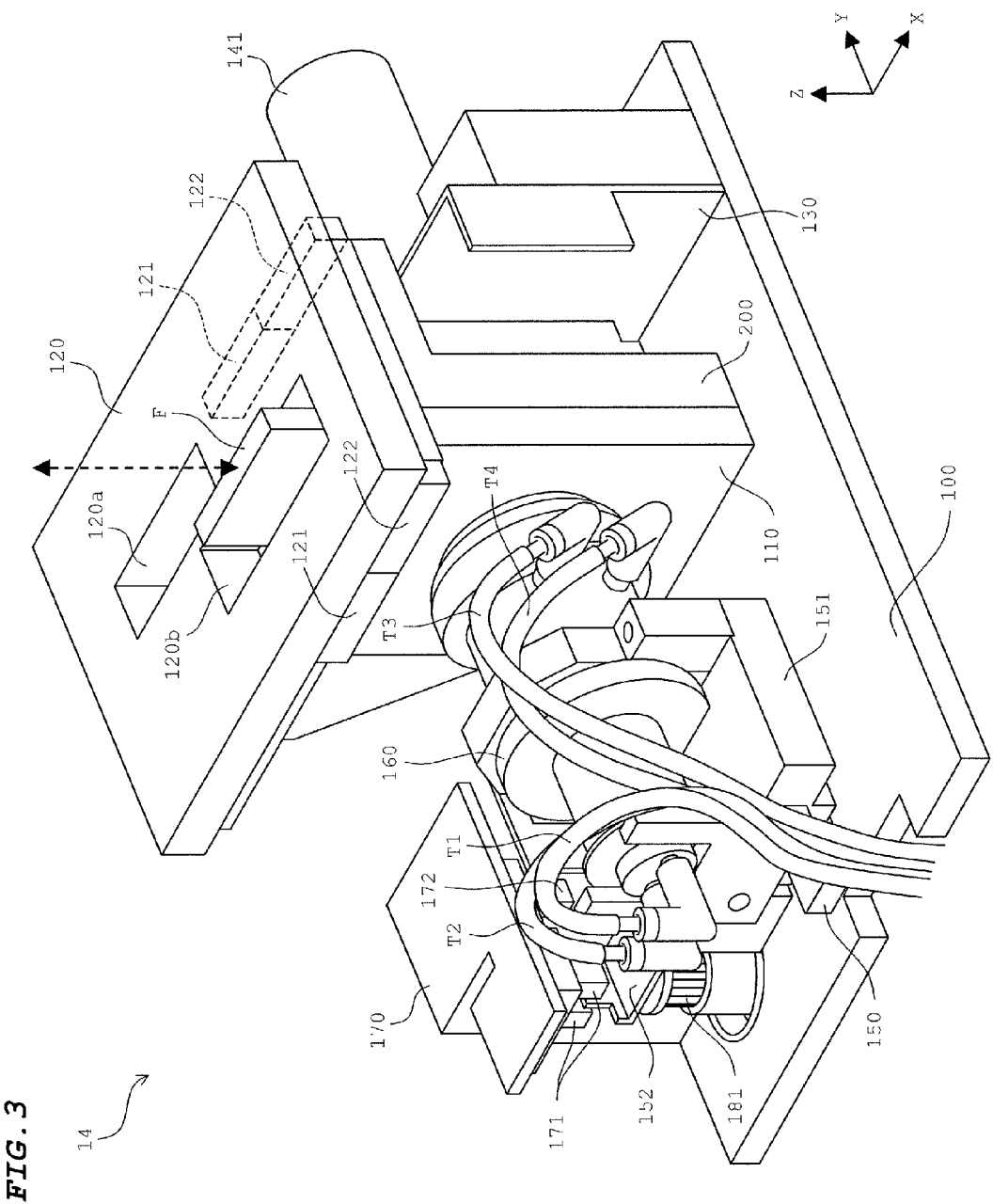
FIG. 3 is a perspective view showing a configuration of a separation/substitution section according to the embodiment.

FIG. 3 is a perspective view showing a configuration of the separation/substitution section 14. In FIG. 3, the Z axis direction is the vertical direction, and the Z axis positive direction and the Z axis negative direction are the upward direction and the downward direction, respectively.

A base 100 is a plate-shaped member which is parallel to the XY plane. On the base 100, a receptacle body 200, support members 110, 130, and 170, and a rail 150 are provided. In addition to these, various mechanisms and the like are provided on the base 100, but in FIG. 3, such mechanisms and the like are not shown for convenience.

The support member 110 is a plate-shaped member which is parallel to the XZ plane. In the support member 110, a hole 111 (see FIG. 10) which passes therethrough in the Y axis direction is formed. On the upper faces of the receptacle body 200 and the support member 110, a top plate 120 is provided. The top plate 120 is located inside the measurement apparatus 2 so as to allow the user to access the top plate 120 when the cover 2b (see FIG. 1) of the measurement apparatus 2 is opened upwardly.

In the top plate 120, holes 120a and 120b which pass therethrough in the up-down direction are formed. Via the hole 120a, the pipette 11a of the specimen pipette section 11 performs aspiration and discharge of a sample with respect to the receptacle 210 of the receptacle body 200 described later. The user opens the cover 2b provided to the measurement apparatus 2, and sets or takes out a filter member F with respect to a receptacle 220 of the receptacle body 200 described later, along the broken line arrow (vertical direction) via the hole 120b.

The top plate 120 is a translucent member, and is provided with sensors 121 and 122 each composed of a light emitter and a light receiver. When the filter member F is correctly set, light emitted from the light emitter of the sensor 121 is blocked by the filter member F, and light emitted from the light emitter of the sensor 122 passes through a cutout F6 (FIGS. 6A and 6B) of the filter member F. When the filter member F is set with its faces F1 and F2 (see FIGS. 6A and 6B) reversed, lights emitted from the light emitters of the sensors 121 and 122 are blocked by the filter member F. Accordingly, whether the filter member F is correctly set can be detected.

The support member 130 supports a motor 141. On the rail 150, a support member 151 is provided so as to be slidable in the Y axis direction. On the support member 151, a flange portion 152 and a piston 160 are provided. To the piston 160, tubes T1 to T4 are connected. The support member 170 is provided with sensors 171 and 172 each composed of a light emitter and a light receiver.

Figure 4B:
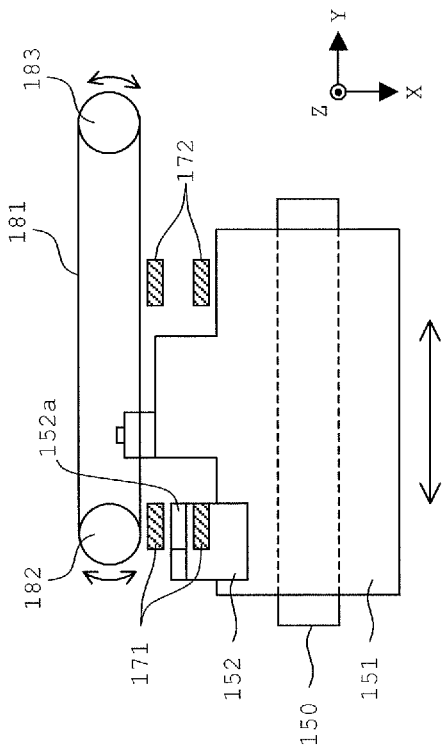
FIGS. 4A and 4B are respectively a side view of a motor and a plan view of a mechanism for driving a piston viewed from above according to the embodiment.
Figure 4A:
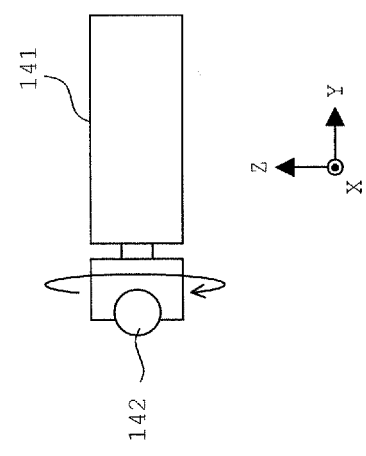

FIG. 4A is a side view of the motor 141. The rotation axis of the motor 141 is parallel to the Y axis, and is aligned with a central axis A described later. At the end on the Y axis negative direction side of the motor 141, a magnet 142 is provided. By the motor 141 being driven and the magnet 142 rotating in the XZ plane, a stirrer R described later is rotated via a wall of the receptacle body 200.

FIG. 4B is a plan view of a mechanism for driving the piston 160 viewed from above. In FIG. 4B, the piston 160 is not shown for convenience. The support member 151 is fixed to a belt 181. The belt 181 is supported by pulleys 182 and 183. The pulley 182 is connected to the rotating shaft of a stepping motor provided on the lower face side of the base 100. When this stepping motor is driven, the support member 151 is caused to slide on the rail 150 in the Y axis direction, and the piston 160 is driven in the Y axis direction. The sensors 171 and 172 are set at positions at which the sensors 171 and 172 can detect a light blocking portion 152a of the flange portion 152 provided on the support member 151. Based on detection signals from the sensors 171 and 172, that the piston 160 is located at the leftmost side and that the piston 160 is located at the rightmost side are detected, respectively.

FIG. 5A is a perspective view showing a configuration of the receptacle body 200. FIG. 5B is a perspective view of the receptacle body 200 cut along a plane including a wall portion 222 in FIG. 5A. FIG. 5C is a side view of the receptacle body 200 shown in FIG. 5B, viewed in the Y axis positive direction.

With reference to FIG. 5A, in the receptacle body 200, the receptacles 210 and 220 are formed. An insertion hole 211 located in an upper portion of the receptacle 210 is connected to the hole 120a of the top plate 120. An insertion hole 221 located in an upper portion of the receptacle 220 is connected to the hole 120b of the top plate 120. The receptacle 220 has the wall portion 222 which is parallel to the XZ plane. In the wall portion 222, a recess 230 in which the stirrer R described later is accommodated is formed. A bottom face 223 of the receptacle 220 has a curved surface, and at the lowest position of the bottom face 223, a hole H21 is formed. The Y axis negative direction side of the receptacle 220 is open.

With reference to FIGS. 5B and 5C, the recess 230 includes: an opening 231 which makes the recess 230 open on the Y axis negative direction side; an inner side face 232 which is circular when viewed in the Y axis direction; a reservoir 233 which is formed in a lower portion of the inner side face 232; and a wall portion 234 which is parallel to the XZ plane. The recess 230 is distanced from the receptacle 210 in a plane view, i.e., in directions (horizontal direction) on the XY plane. The central axis A indicated by the dotted line in FIG. 5B is an axis that passes the center of a circular shape of the inner side face 232 when viewed in the Y axis direction and that is parallel to the Y axis direction. The reservoir 233 is formed in the inner side face 232 so as to be recessed in a direction away from the central axis A. At the lowest position of the reservoir 233, a hole H22 is formed. In the wall portion 234, a hole H23 is formed at a position where the central axis A crosses the wall portion 234.

The receptacle 210 has a shape whose inside is gradually narrowed in the depth direction (downward direction). In an upper portion of the inner side face of the receptacle 210, holes H11 to H13 are formed. In a deepest portion of the receptacle 210, holes H14 and H15 are formed. The hole H14 is connected, via a flow path 241, to the hole H22 of the reservoir 233. The hole H15 is connected, via a flow path 242, to a hole H16 formed in the outer face of the receptacle body 200. Arrangement among the receptacle 210, the recess 230, and the flow path 241 is adjusted such that the hole H14 is located lower than the hole H22. It should be noted that the hole H16 is connected to a valve V25 (see FIG. 12), and the diameter of the flow path 242 is sufficiently small. Thus, the sample held in the receptacle 210 does not flow downwardly from the hole H15.

In the receptacle 210, pins 212 to 214 are provided. The pins 212 to 214 are connected to a liquid level sensor section 293 (see FIG. 13) of a resistance-type. The liquid level sensor section 293 detects, based on the energized states of the pins 212 and 214, whether the level of the liquid held in the receptacle 210 is above the height position of the pin 212, and detects, based on the energized states of the pins 213 and 214, whether the level of the liquid held in the receptacle 210 is above the height position of the top of the pin 213.

Figure 6A:
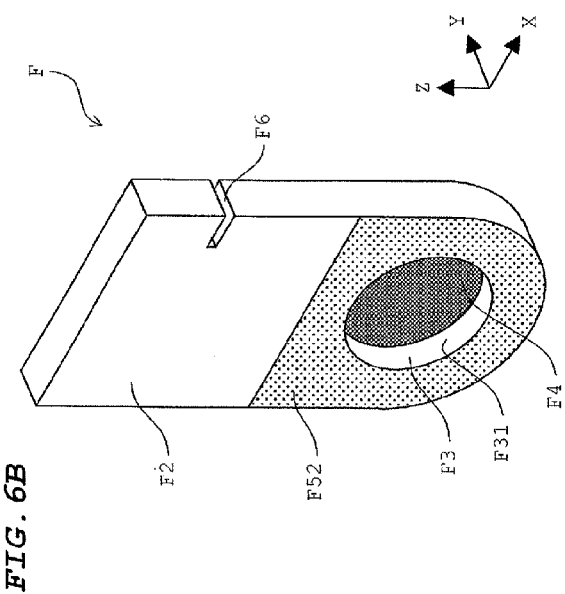
FIGS. 6A to 6D are perspective views showing a configuration of a filter member and perspective views showing a configuration of a stirrer, according to the embodiment.
Figure 6B:
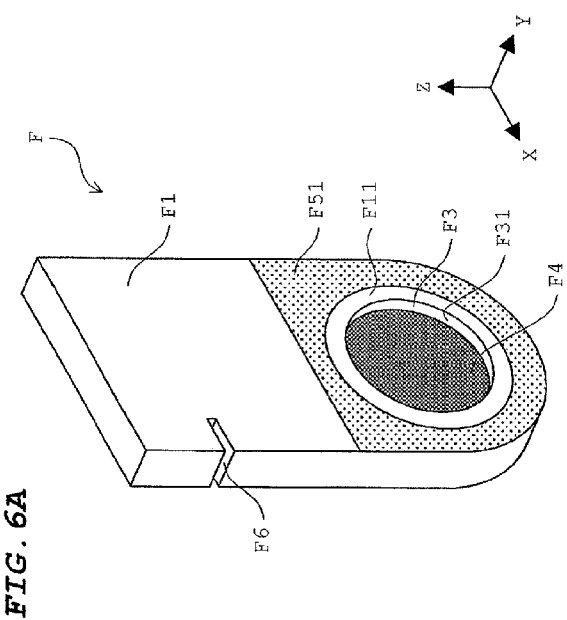

FIGS. 6A and 6B are perspective views showing a configuration of the filter member F. FIGS. 6A and 6B also show coordinate axes of a state where the filter member F is appropriately set in the receptacle 220.

The filter member F includes: the faces F1 and F2 which are parallel to the XZ plane; a hole F3 passing through the filter member F in the Y axis direction; a filter F4; a rubber F51 having a thin-film shape provided on the face F1; and a rubber F52 having a thin-film shape provided on the face F2. The faces F1 and F2 are on the Y axis positive direction side and the Y axis negative direction side, respectively. The hole F3 includes an inner side face F31 having a cylindrical shape.

The filter F4 is set to the inner side face F31 of the hole F3 such that the filtering face thereof is parallel to the XZ plane. The filter F4 has holes having a diameter that allows a cell or the like (red blood cell, white blood cell, bacterium, or contaminant) having a diameter smaller than the diameter of an analysis target cell (epidermal cell of the uterine cervix) to pass therethrough, and that does not allow an analysis target cell to pass therethrough.

The size of an epidermal cell of the uterine cervix is about 20 to 80 μm (about 60 μm in average). The size of a red blood cell, which is a cell smaller than the measurement target cell, is about 7 to 10 μm. Similarly, the size of a white blood cell, which is a cell smaller than the measurement target cell, is about 8 to 15 μm. Further, the size of a contaminant such as a bacterium is about 1 to several μm.

Thus, the filter F4 in the present embodiment is made of metal, and has holes having a diameter that is greater than or equal to 8 μm and smaller than 20 μm so as not to allow epidermal cells to pass through the holes of the filter F4. When the diameter of each hole is smaller than 8 μm, a phenomenon where cells and contaminants are clogged in the holes is often observed. When the diameter of each hole is greater than or equal to 20 μm, there is a risk that epidermal cells pass through the holes of the filter F4. Preferably, the diameter of each hole of the filter F4 is about 10 μm.

Such a filter can be made by a known method, and can be made by, for example, an electro fine forming technology or CVD (chemical vapor deposition).

In the Y axis direction, the distance between the filter F4 and the face F1 is smaller than the distance between the filter F4 and the face F2. The rubber F51 is provided around the opening on the face F1 side of the hole F3. Between the opening on the face F1 side of the hole F3 and the rubber F51, a face F11 being a part of the face F1 is exposed. The rubber F52 is provided around the opening on the face F2 side of the hole F3.

In more detail, the filter member F shown in FIGS. 6A and 6B are configured as shown in FIG. 7A to FIG. 8E. In the following, with reference to FIG. 7A to FIG. 8E, the detailed configuration of the filter member F will be described.

FIG. 7A is an exploded view of the filter member F, FIG. 7B shows a configuration of an end portion on the Z axis negative direction side of a holding member F100, and FIG. 7C shows a configuration of a holding member F200. FIGS. 8A and 8B show states where the filter F4 is sandwiched by the holding members F100 and F200. FIGS. 8C and 8D show the filter member F that has been completed. FIG. 8E is a cross-sectional view of the filter member F cut along a face that is inclined by 45 degrees relative to the X axis and the Z axis.

As shown in FIG. 7A, the filter member F includes: the holding member F100 having a plate-like shape; the holding member F200 which is round; the filter F4 having a circular shape; and the rubbers F51 and 52 each having a ring shape. As shown in FIGS. 7A and 7B, on the Y axis negative direction side in a lower portion (Z axis negative direction side) of the holding member F100, a recess F110 having a face F111 recessed relative to the face therearound is formed. In the center of the face F111, a hole F120 passing through the holding member F100 in the Y axis direction is formed. The hole F120 includes an inner side face F121 having a cylindrical shape. In the outer periphery of the face F111, four holes F130 passing through the holding member F100 in the Y axis direction are formed.

As shown in FIG. 7B and FIG. 8E, the face on the outer periphery side of each hole F130 is shaped so as to be recessed outwardly relative to the inner wall of the recess F110. Accordingly, a step is formed in the inner wall of the recess F110, and this step serves as an engagement portion F131 which engages with a stopper F231 described later. It should be noted that each hole F130 passes through the recess F110 to the back surface of the holding member F100. This is caused by pulling out the die portion for forming the engagement portion F131 in the Y axis positive direction, at the time of molding the holding member F100. That is, by causing each hole F130 to pass through the holding member F100 to the back surface thereof in this manner, it is possible to easily form each engagement portion F131.

As shown in FIGS. 7A and 7B, in the outer periphery on the Y axis negative direction side of the hole F120, an elastic body F140 is molded by two-color molding. The upper face of the elastic body F140 is recessed relative to the face F111. In addition, the outer diameter of the elastic body F140 is substantially the same as the outer diameter of the filter F4. Thus, when assembling the filter member F, it is possible to position the filter F4 only by placing the filter F4 on the elastic body F140.

As shown in FIG. 8A, in the outer periphery on the Y axis positive direction side of the hole F120, a face F151 having an annular shape is formed. In the outer periphery of the face F151, a face F152 recessed relative to the face F151 is formed. The outer diameter of the face F151 is substantially the same as the diameter of a hole F51a of the rubber F51. Thus, when assembling the filter member F, it is possible to position the rubber F51 only by placing the rubber F51 on the face F152.

As shown in FIG. 7A and FIG. 8A, in the holding member F100, a face F101 recessed relative to the face therearound is formed. Thus, in the holding member F100, the thickness near an upper end portion F102 which is distanced in the Z axis positive direction (longitudinal direction) from the position where the filter F4 is mounted is greater than the thickness of the portion of the face F101 which is on the inner side in the longitudinal direction (Z axis negative direction side) relative to the upper end portion F102. In addition, as shown in FIG. 3, it is configured such that, when the filter member F is mounted to the receptacle 220, the upper end portion F102 protrudes above the hole 120b of the top plate 120, together with an upper portion of the filter member F. As described above, in the end portion on the X axis positive direction side of the holding member F100, the cutout F6 passing through the holding member F100 in the Y axis direction is formed.

As shown in FIGS. 7A and 7C, on the Y axis negative direction side of the holding member F200, a face F210 which is parallel to the XZ plane is formed. In the center of the face F210, a hole F220 which is circular and which passes through the holding member F200 in the Y axis direction is formed. The hole F220 includes an inner side face F221 having a cylindrical shape. The diameter of the hole F220 is substantially the same as the diameter of a hole F52a of the rubber F52. On the Y axis positive direction side of the holding member F200, four projecting pieces F230 are formed. At an end of each projecting piece F230, a stopper F231 protruding toward the outer periphery side is formed.

In the outer periphery on the Y axis positive direction side of the hole F220, an elastic body F240 is molded by two-color molding. The upper face of the elastic body F240 is raised relative to the face therearound of the elastic body F240. The outer diameter of the elastic body F240 is substantially the same as the outer diameter of the filter F4.

As shown in FIG. 7A, the filter F4 is composed of a center portion F41 and a thick portion F42. As described above, the center portion F41 has holes having a diameter that allows a cell or the like (red blood cell, white blood cell, bacterium, or contaminant) having a diameter smaller than the diameter of an analysis target cell (epidermal cell of the uterine cervix) to pass therethrough, and that does not allow an analysis target cell to pass therethrough. The thickness of the center portion F41 is about 10 µm. The thick portion F42 is formed by electroforming in the outer periphery of the center portion F41. The thickness of the thick portion F42 is configured so as to be greater than the thickness of the center portion F41, and is about 0.1 mm.

The rubbers F51 and F52 have the holes F51a and F52a formed in the centers thereof, respectively. The outer diameters of the rubbers F51 and F52 are substantially the same as the outer diameter of the face F152 of the holding member F100 and the outer diameter of the holding member F200, respectively.

When the filter member F is to be assembled, first, the filter F4 is placed on the elastic body F140 of the holding member F100. At this time, the thick portion F42 of the filter F4 comes into contact with the elastic body F140. Subsequently, the holding member F200 is fitted into the recess F110 of the holding member F100 such that the projecting pieces F230 of the holding member F200 face the holes F130 of the holding member F100, respectively. At this time, the projecting pieces F230 come into contact with the inner wall of the recess F110 and elastically deform inwardly. Thereafter, when the stoppers F231 of the projecting pieces F230 reach the positions of the engagement portions F131, respectively, the projecting pieces F230 elastically return outwardly as shown in FIG. 8E, whereby the stoppers F231 engage with the engagement portions F131, respectively. Accordingly, the thick portion F42 of the filter F4 is sandwiched by the elastic bodies F140 and F240. In this manner, as shown in FIGS. 8A and 8B, the filter F4 is sandwiched by the holding members F100 and F200.

Next, the rubber F51 is attached to the face F152 of the holding member F100 by means of a double-sided adhesive tape, and the rubber F52 is attached to the face F210 of the holding member F200 by means of a double-sided adhesive tape. Accordingly, as shown in FIGS. 8C and 8D, the filter member F is completed.

In FIGS. 6A and 6B, the face F11 corresponds to the face F151 of the holding member F200. The hole F3 is formed by the hole F120 of the holding member F100 and the hole F220 of the holding member F200. The inner side face F31 is formed by the inner side face F121 of the holding member F100 and the inner side face F221 of the holding member F200. In the following, description will be given, using the filter member F shown in FIGS. 6A and 6B for convenience.

Figure 6C:
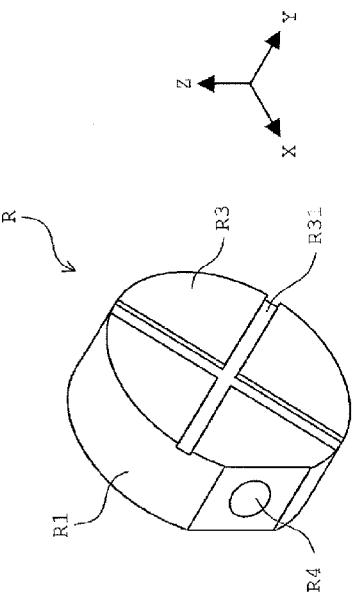
Figure 6D:
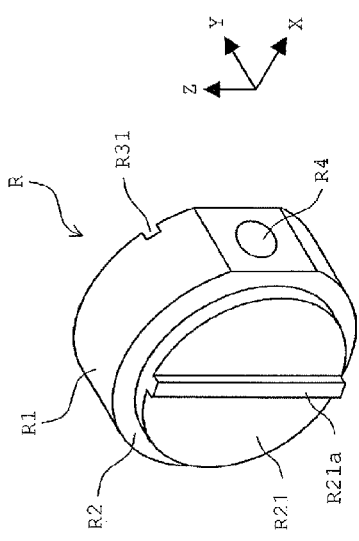

FIGS. 6C and 6D are perspective views showing a configuration of the stirrer R. FIGS. 6C and 6D also show coordinate axes of a state where the stirrer R is accommodated in the recess 230.

The stirrer R includes: a barrel portion R1 having a cylindrical shape; faces R2 and R3 which are parallel to the XZ plane; and a magnet R4. The faces R2 and R3 are on the Y axis negative direction side and the Y axis positive direction side, respectively. On the face R2, a protrusion R21 having a cylindrical shape that protrudes in the Y axis negative direction side relative to the face R2 is formed. The diameter of the protrusion R21 is smaller than the outer diameter of the face R2. In addition, on the protrusion R21, a flange portion R21a is formed. In the face R3, grooves R31 which cross each other at the center of the face R3 are formed. The magnet R4 is provided so as to pass the center of the stirrer R and pass through the stirrer R in the XZ plane. Accordingly, when the magnet 142 shown in FIG. 4A is rotated by the motor 141, the stirrer R rotates about the Y axis.

Figure 9A:
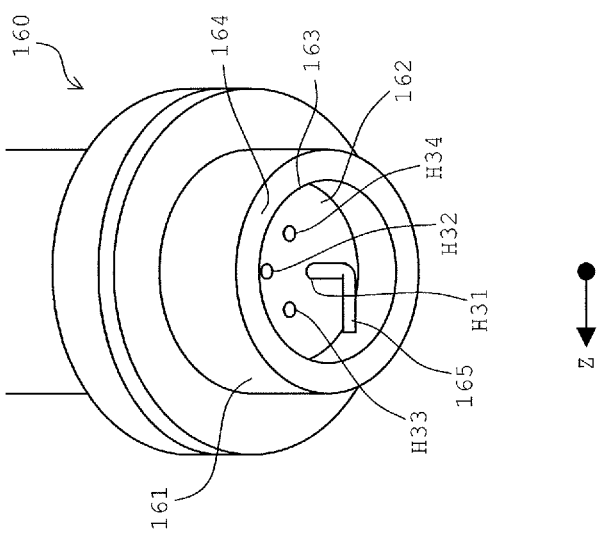
FIGS. 9A and 9B are respectively a side view and a perspective view showing a configuration of the piston according to the embodiment.
Figure 9B:
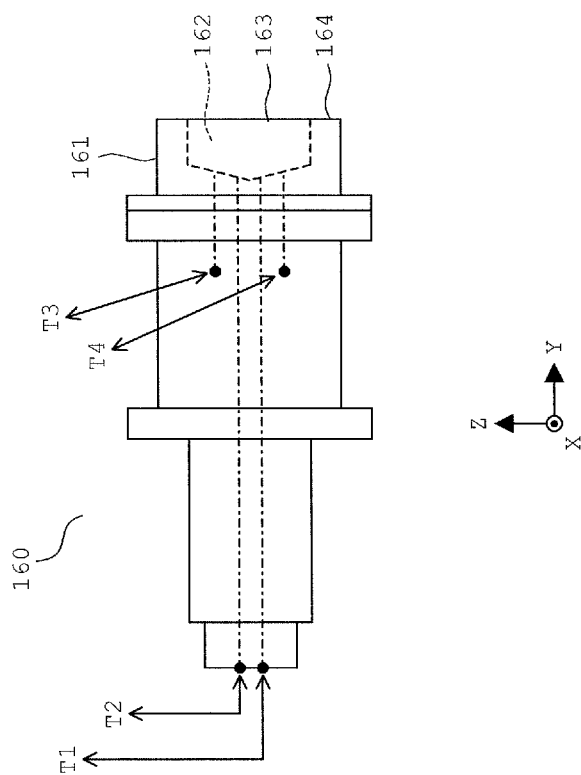

FIGS. 9A and 9B are a side view and a perspective view showing a configuration of the piston 160.

The piston 160 has a leading end portion 161 having a cylindrical shape on the Y axis positive direction side. On the Y axis positive direction side of the leading end portion 161, a recess 162, an opening 163 which makes the recess 162 open on the Y axis positive direction side, and a face 164 are formed. On the face on the Y axis negative direction side of the recess 162, holes H31 to H34 are formed. The holes H31 to H34 are respectively connected to the tubes T1 to T4 via flow paths provided inside the piston 160. To the hole H31, a pipe 165 of an L-shape is connected. The leading end of the pipe 165 is located in an upper portion (Z axis positive direction side) in the recess 162. The face 164 is parallel to the XZ plane, and is formed around the opening 163.

Figure 10:
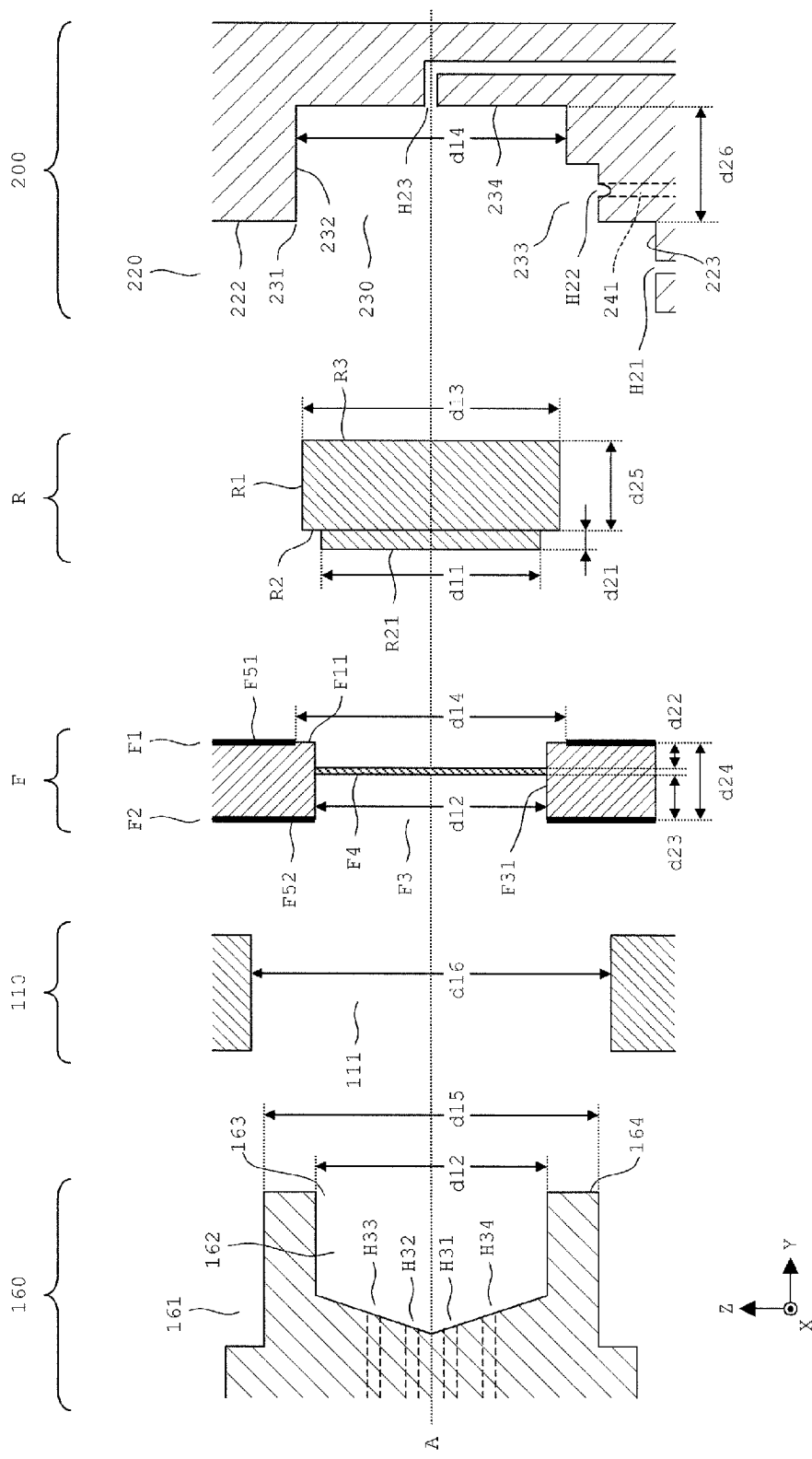
FIG. 10 is cross-sectional views of the piston, a support member, the filter member, the stirrer, and the receptacle body according to the embodiment, when they are cut along a plane that passes a central axis.

FIG. 10 shows cross-sectional views of the piston 160, the support member 110, the filter member F, the stirrer R, and the receptacle body 200, cut along the YZ plane that passes the central axis A. For convenience, FIG. 10 shows the respective members spaced from each other in the Y axis direction. d11 to d16 denote the lengths in the Z axis direction, respectively, and the magnitude of their values increases in this order. d21 to d26 denote the lengths in the Y axis direction, respectively, and the magnitude of their values increases in this order.

In the piston 160, the diameter of the recess 162 is d12, and the outer diameter of the face 164 is d15. In the support member 110, the diameter of the hole 111 is d16. In the filter member F, the diameter the hole F3 is d12, the outer diameter of the face F11 is d14, the interval between the face F1 and the filter F4 is d22, the interval between the face F2 and the filter F4 is d23, and the interval between the faces F1 and F2 is d24. In the stirrer R, the diameter of the barrel portion R1 is d13, the diameter of the protrusion R21 is d11, the width of the barrel portion R1 is d25, and the width of the protrusion R21 including the flange portion R21a is d21. In the receptacle body 200, the diameter of the inner side face 232 is d14, and the width of the recess 230 is d26.

In the case of the filter member F shown in FIG. 7A to FIG. 8E, the diameter of each of the holes F120 and F220 is d12, the outer diameter (the diameter of the hole F51a of the rubber F51) of the face F151 is d14, the interval between the face F151 and the filter F4 is d22, the interval between the upper face of the rubber F52 and the filter F4 is d23, and the interval between the upper face of the rubber F51 and the upper face of the rubber F52 is d24.

It should be noted that each of the recess 162, the outer circumference of the face 164, the hole 111, the hole F3, the outer circumference of the face F11, the barrel portion R1, the protrusion R21, and the recess 230 when viewed in the Y axis direction has a circular shape. The centers of these circular shapes are aligned with the central axis A.

FIGS. 11A to 11D illustrate a procedure of setting the filter member F in the receptacle 220. FIGS. 11A to 11D are cross-sectional views similar to those in FIG. 10.

FIG. 11A shows a state where the filter member F has not yet been set in the receptacle 220. At this time, the piston 160 is located at the leftmost side, and the face R3 of the stirrer R is in contact with the wall portion 234 by being pulled in the right direction by the magnet 142 (see FIG. 4A). From the state of FIG. 11A, when the filter member F is inserted into the receptacle 220 through the hole 120b of the top plate 120 and the insertion hole 221 of the receptacle 220, the state shown in FIG. 11B is established. At this time, the filter member F is supported in the upward direction by the bottom face 223 of the receptacle 220.

From the state shown in FIG. 11B, when the piston 160 is located at the rightmost side, then, as shown in FIG. 11C, the face 164 of the piston 160 is pushed against the rubber F52 of the filter member F, and the rubber F51 of the filter member F is pushed against the wall portion 222 of the receptacle 220. Accordingly, the recess 230 and the recess 162 are connected to each other via the filter F4. At this time, by the opening 231 of the recess 230 being closed by the filter member F, a space S1 which is closed from the outside is formed. In addition, by the opening 163 of the recess 162 being closed by the filter member F, a space S2 which is closed from the outside is formed.

Specifically, the space S1 is formed by the side face on the recess 230 side of the filter F4, the inner side face F31, the face F11, the rubber F51, the inner side face 232, the reservoir 233, and the wall portion 234. At this time, the space S1 is connected to the outside structurally, via the holes H22 and H23. However, during the process of separation/substitution, the sample is reserved in the deepest portion, of the receptacle 210, that is located at the lower end of the flow path 241 extending from the hole 1122. Therefore, the hole H22 is in a substantially closed state. In addition, the flow path extending from the hole H23 is provided with a valve V24 (see FIG. 12) which can close this flow path, and through the hole H23, only the diluent flows into the space S1 from the outside. Therefore, the hole H23 is in a substantially closed state. Accordingly, the space S1 becomes a space closed from the outside.

In addition, as described above, the filter F4 has holes having a diameter that allows a cell or the like having a diameter smaller than the diameter of an analysis target cell to pass therethrough, and that does not allow an analysis target cell to pass therethrough. Accordingly, cells and the like having diameters smaller than the diameters of analysis target cells in the space S1 will pass through the filter F4, but analysis target cells in the space S1 will remain in the space S1.

The space S2 is specifically formed by: the side face, on the opposite side to the recess 230, of the filter F4; the inner side face F31; the rubber F52; and the recess 162. At this time, the space S2 is connected to the outside structurally, via the holes H31 to H34. However, the flow paths extending from the holes H31 to H34 are provided with valves that can respectively close these flow paths, and thus, the holes H31 to H34 are in substantially closed states. Accordingly, the space S2 becomes a space closed from the outside.

In the state shown in FIG. 11C, by the magnet 142 (see FIG. 4A) being rotated, the stirrer R is rotated about the central axis A along the side face (filtering face) on the recess 230 side of the filter F4. At this time, as shown in FIG. 6D, the face R3 of the stirrer R has the grooves R31 formed therein. Thus, the diluent smoothly flows from the hole H23 into the space S1.

There are cases where, while the stirrer R is being rotated by the magnet 142, the stirrer R is moved toward the filter member F away from the wall portion 234 as shown in FIG. 11D. However, as shown in FIG. 10, the width d21 of the protrusion R21 including the flange portion R21a is smaller than the interval d22 between the face F11 and the filter F4, the diameter d11 of the protrusion R21 is smaller than the diameter d12 of the hole F3, and the outer diameter d13 of the face R2 (the barrel portion R1) is greater than the diameter d12 of the hole F3. Accordingly, as shown in FIG. 11D, the face R2 abuts against the face F11, and thus, it is possible to prevent damage of the filter F4 which may be caused by the protrusion R21 including the flange portion R21a coming into contact with the filter F4.

Figure 12:
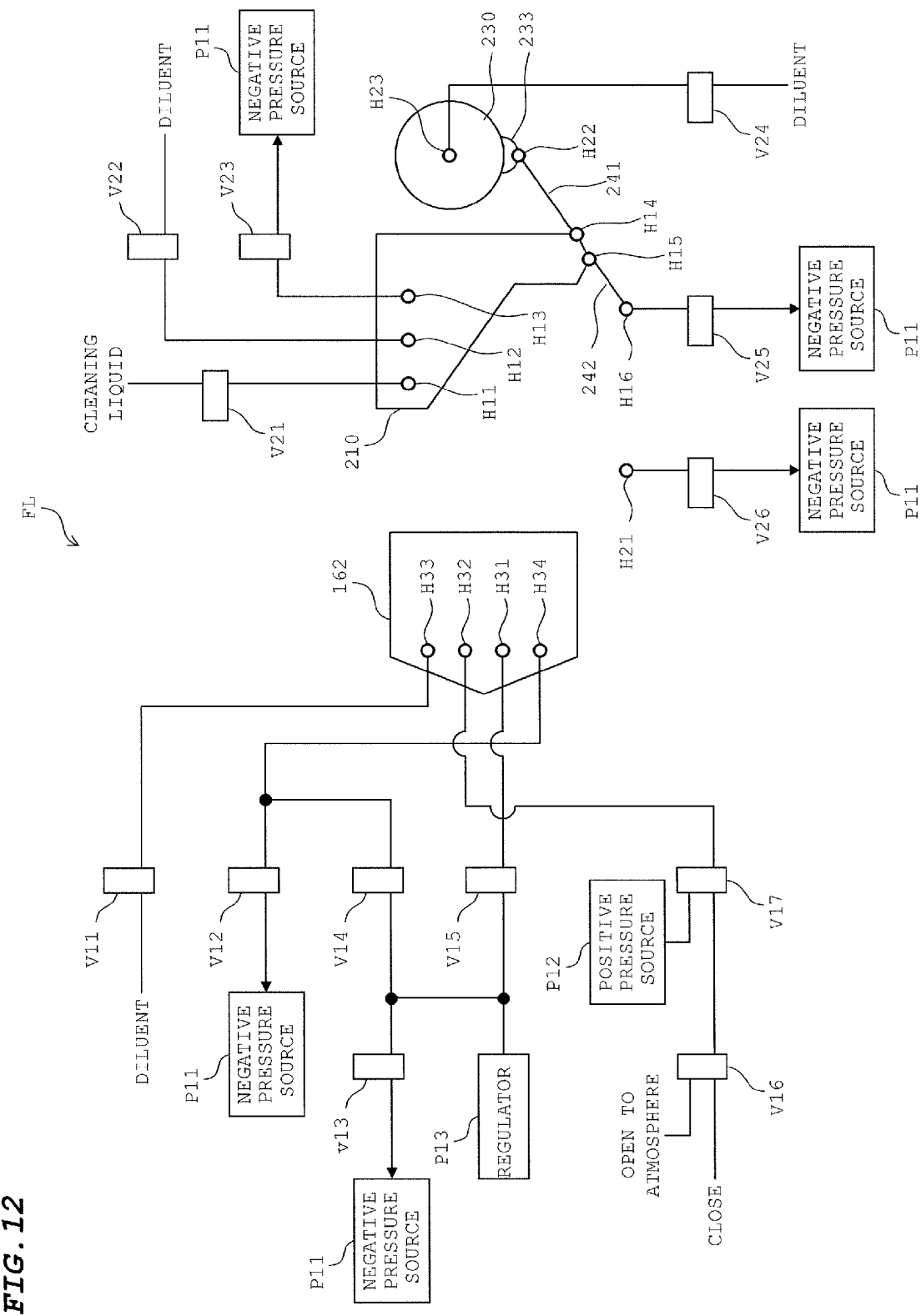
FIG. 12 shows a fluid processing section of the measurement apparatus according to the embodiment.

FIG. 12 shows a fluid processing section FL of the measurement apparatus 2.

Valves V11 to V15 and V21 to V26 are each configured to be switchable between a state of opening a flow path and a state of closing the flow path. Valves V16 and V17 are each configured to be able to connect either one of flow paths connected thereto on the left side, to the single flow path on the right side. The holes H31 to H34 are connected to the valve V15, the valve V17, the valve V11, and the valves V12 and V14, respectively. The holes H11 to H13 are connected to the valves V21 to V23, respectively. The holes H23, H16, and H21 are connected to the valves V24, V25, V26, respectively. A negative pressure source P11 is connected to each of the valves V12, V13, V23, V25, and V26, and a positive pressure source P12 is connected to the valve V17. A regulator P13 for keeping the pressure constant is connected to the valves V13 to V15. The drive of the fluid processing section FL and the flow of the fluid in the fluid processing section FL will be described later with reference to FIG. 15.

Figure 13:
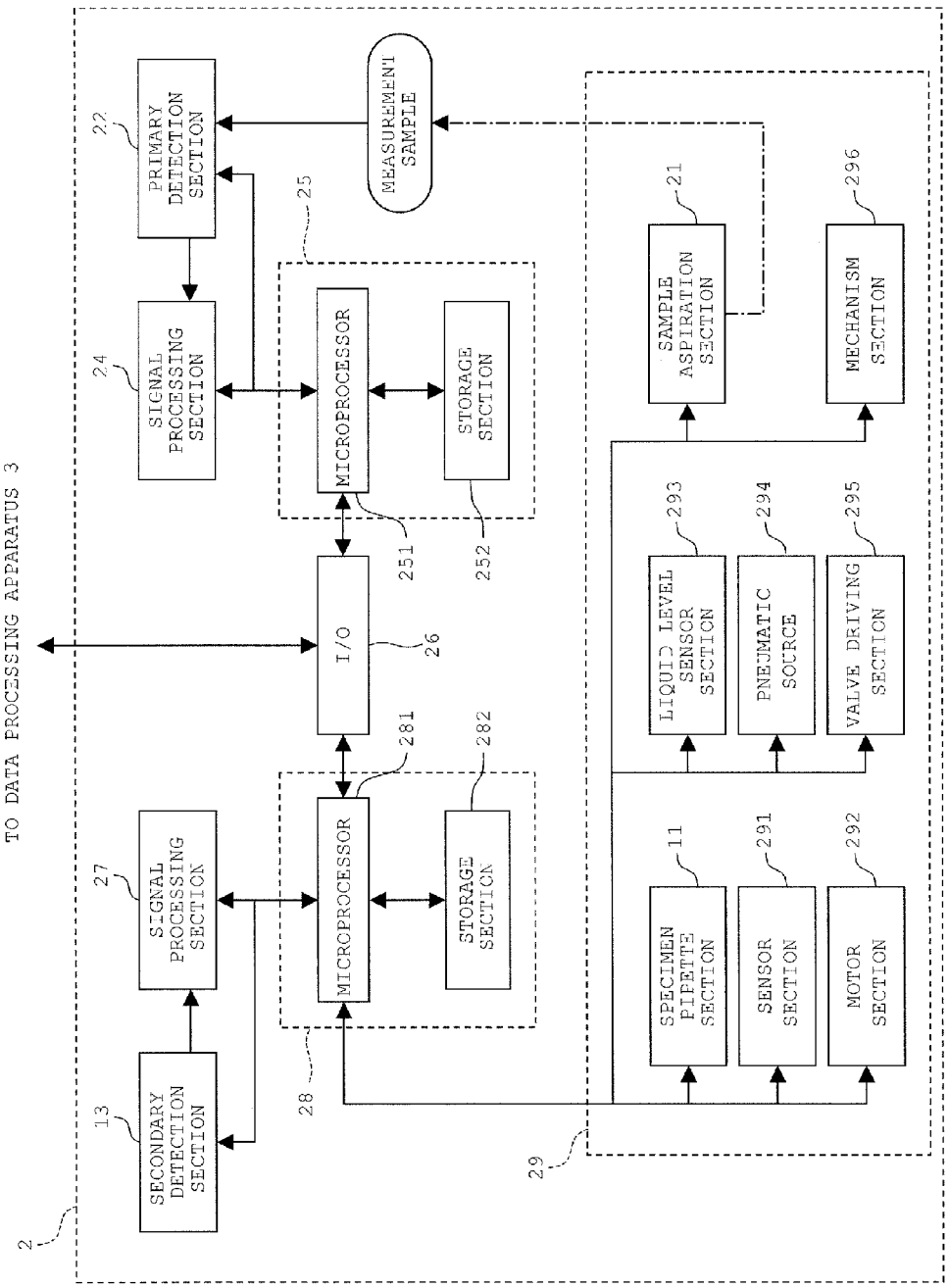
FIG. 13 shows a configuration of the measurement apparatus according to the embodiment.

FIG. 13 shows a configuration of the measurement apparatus 2.

The measurement apparatus 2 includes the primary detection section 22 and the secondary detection section 13 shown in FIG. 2, and a preparation device section 29 including sections for automatically performing preparation of a sample as described above. The measurement apparatus 2 also includes a signal processing section 24, a measurement control section 25, an I/O interface 26, a signal processing section 27, and a preparation control section 28.

The primary detection section 22 outputs a forward scattered light signal (FSC), a side scattered light signal (SSC), and a side fluorescence signal (SFL) based on a measurement sample. The signal processing section 24 processes the signals FSC, SSC, and SFL outputted from the primary detection section 22, and outputs the resultant signals to the measurement control section 25. The measurement control section 25 includes a microprocessor 251 and a storage section 252. The microprocessor 251 is connected to the data processing apparatus 3 and the preparation control section 28, via the I/O interface 26. The signals FSC, SSC, and SFL are transmitted by the microprocessor 251 to the data processing apparatus 3.

The data processing apparatus 3 obtains characteristic parameters such as forward scattered light intensity and side fluorescence intensity based on the signals FSC, SSC, and SFL, and based on these characteristic parameters, creates frequency distribution data for analyzing cells and nuclei. Then, based on this frequency distribution data, the data processing apparatus 3 performs a discrimination process of particles in the measurement sample, and determines whether the analysis target cells are abnormal, specifically, whether the analysis target cells are cancerous cells (atypical cells).

The secondary detection section 13 is configured to obtain forward scattered light signals (FSC), and outputs signals for counting the number of cells having the sizes that correspond to surface layer cells and middle layer cells based on the signals FSC. The signal processing section 27 processes the signals FSC outputted from the secondary detection section 13, and outputs the resultant signals to the preparation control section 28. The preparation control section 28 includes a microprocessor 281 and a storage section 282. The microprocessor 281 is connected to the preparation device section 29, and is connected to the data processing apparatus 3 and the measurement control section 25 via the I/O interface 26.

The preparation device section 29 includes a sensor section 291, a motor section 292, the liquid level sensor section 293, a pneumatic source 294, a valve driving section 295, and the specimen pipette section 11 and the sample aspiration section 21 shown in FIG. 2. A mechanism section 296 includes other mechanisms shown in FIG. 2. The respective sections in the preparation device section 29 are controlled by the preparation control section 28, and signals outputted from the respective sections in the preparation device section 29 are outputted to the preparation control section 28.

The sensor section 291 includes the sensors 121, 122, 171, and 172 shown in FIG. 3. The motor section 292 includes the motor 141 shown in FIG. 4A, and the stepping motor connected to the pulley 182 shown in FIG. 4B. The liquid level sensor section 293 is connected to the pins 212 to 214 shown in FIG. 5C. The pneumatic source 294 includes the negative pressure sources P11, the positive pressure source P12, and positive pressure sources for flowing liquids (diluent, cleaning liquid, and the like) in the fluid processing section FL. The valve driving section 295 includes mechanisms for electromagnetically driving the regulator P13 and the valves in the fluid processing section FL shown in FIG. 12.

Figure 14:
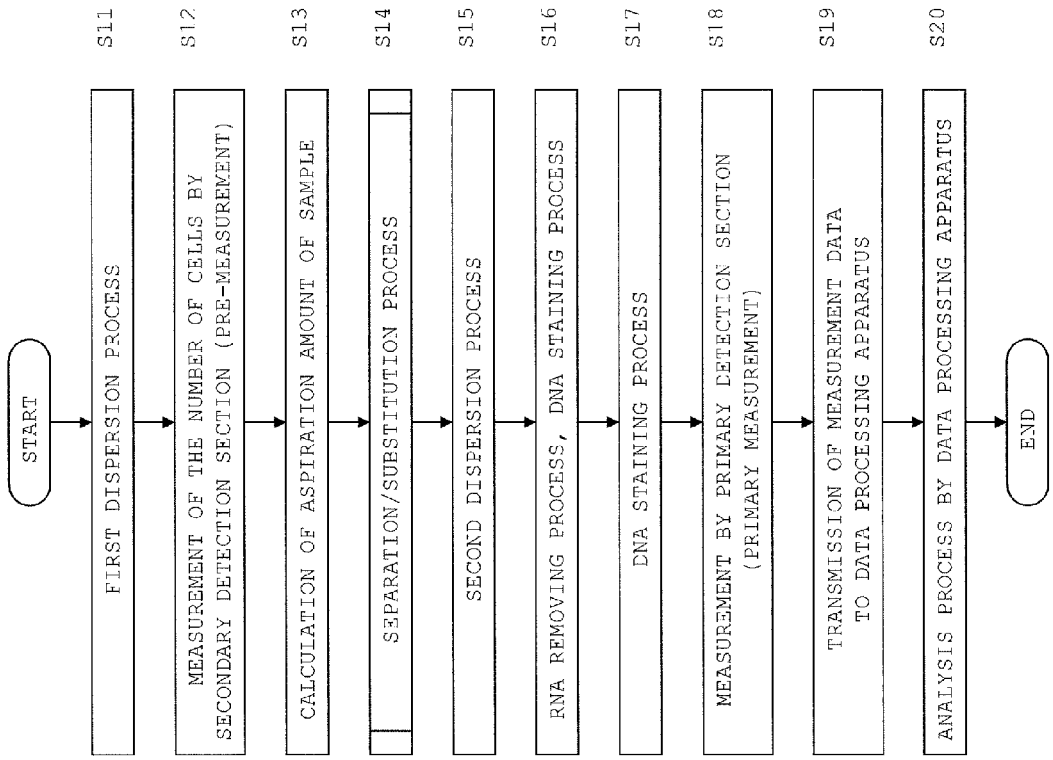
FIG. 14 is a flow chart showing analysis operation performed by the canceration information providing apparatus according to the embodiment.

FIG. 14 is a flow chart showing analysis operation performed by the canceration information providing apparatus 1.

Prior to analysis performed by the canceration information providing apparatus 1, a sample container 4 containing a mixed liquid (sample) composed of cells collected from a subject and a preservative liquid whose major component is methanol is set in the specimen setting section 2a (see FIG. 2) by a user, and then, analysis by the canceration information providing apparatus 1 is started.

When measurement is started, the preparation control section 28 of the measurement apparatus 2 causes the first dispersion section 12 to perform the first dispersion process on aggregated cells in the sample (S11). When the first dispersion process ends, the preparation control section 28 causes the secondary detection section 13 to perform detection (pre-measurement) of the number of analysis target cells (S12), to calculate the concentration of this sample, based on the number of analysis target cells obtained through the pre-measurement and the volume of the sample supplied to the secondary detection section 13. Then, based on the calculated concentration, the preparation control section 28 determines an aspiration amount of the sample necessary for the primary measurement to be performed (S13). Subsequently, the preparation control section 28 causes the separation/substitution section 14 to perform a separation/substitution process (S14). The separation/substitution process will be described later with reference to FIG. 15.

Next, the preparation control section 28 causes the second dispersion section 16 to perform the second dispersion process on aggregated cells in the sample (S15). Subsequently, the preparation control section 28 causes the first reagent adding section 19 to add a reagent (RNase) to the sample, and causes the reaction section 18 to heat a measurement sample container 5 containing this sample, thereby to perform the RNA removing process on the analysis target cells in the measurement sample container 5 (S16). Subsequently, the preparation control section 28 causes the second reagent adding section 20 to add a reagent (staining liquid) to the sample, and causes the reaction section 18 to heat the measurement sample container 5 containing this sample, thereby to perform the DNA staining process on the analysis target cells in the measurement sample container 5 (S17).

Next, the preparation control section 28 causes the sample aspiration section 21 to aspirate the measurement sample having been subjected to the DNA staining process and to send the aspirated measurement sample to the primary detection section 22, and the measurement control section 25 causes the primary detection section 22 to perform the primary measurement on the cells in the measurement sample (S18). The measurement control section 25 transmits measurement data obtained through the primary measurement to the data processing apparatus 3 (S19). Upon receiving the measurement data from the measurement apparatus 2, the data processing apparatus 3 performs an analysis process based on the received measurement data (S20), and displays an analysis result on the display section 32.

Figure 15:
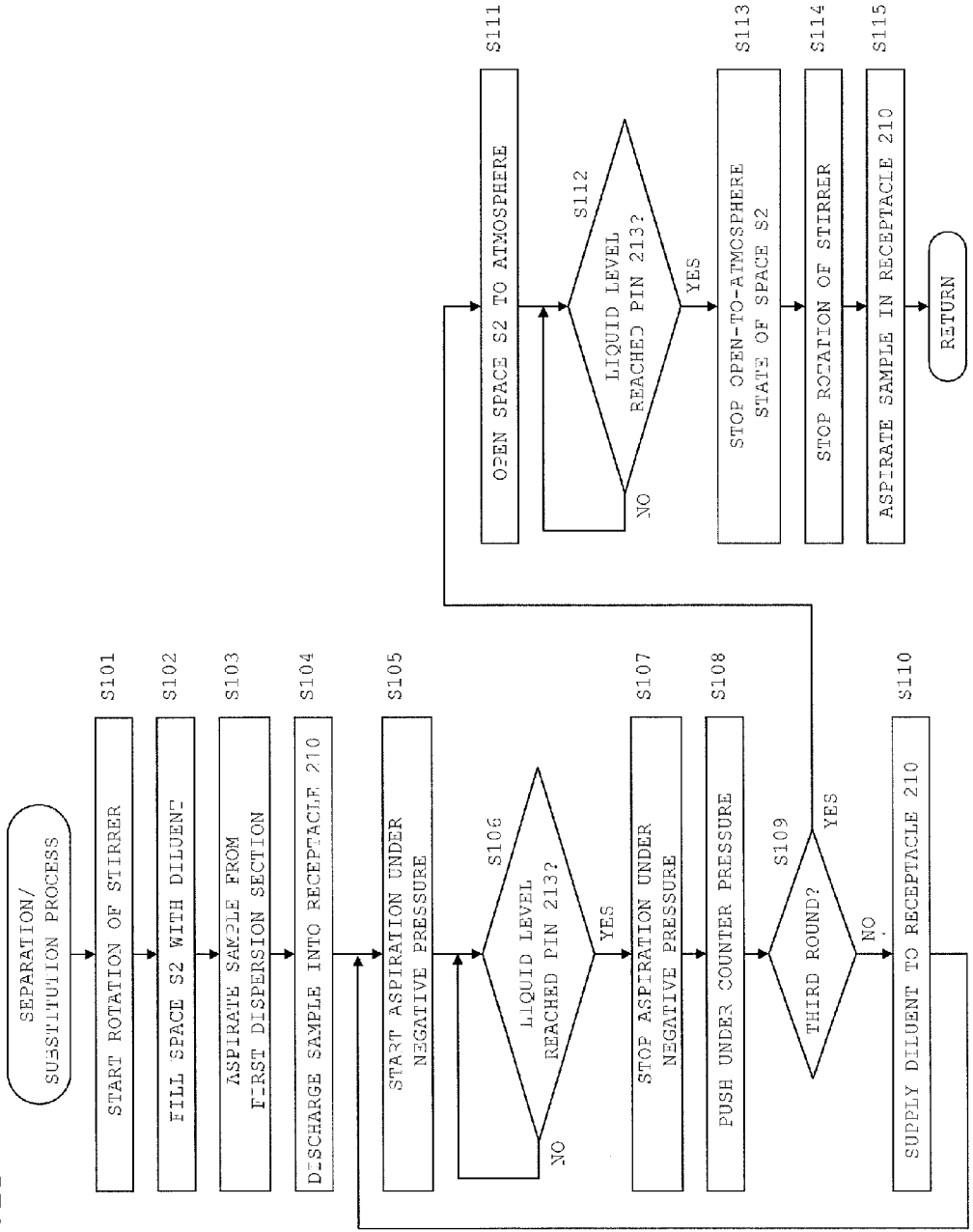
FIG. 15 is a flow chart showing a separation/substitution process according to the embodiment.

FIG. 15 is a flow chart showing the separation/substitution process. FIGS. 16A to 16I are schematic diagrams showing states of the liquid in the receptacle 210 and the spaces S1 and S2.

At the start of the separation/substitution process, the piston 160 and the filter member F are in the state shown in FIG. 11C, and the insides of the receptacle 210 and the spaces S1 and S2 are cleaned. With reference to FIG. 12, in the cleaning operation, the diluent is supplied into the spaces S1 and S2 through the holes H23 and H33, respectively, and the cleaning liquid and the diluent are supplied into the receptacle 210 through the holes H11 and H12, respectively. The waste liquid in the space S1 is sent to the receptacle 210 through the holes H22 and H14. The waste liquid in the receptacle 210 is discarded through the holes H13, H15, and H16. The waste liquid in the space S2 is discarded through the holes H31 and H34. Accordingly, the state of the liquid becomes the state shown in FIG. 16A.

The preparation control section 28 closes the valves V11 to V15 and V21 to V26, closes the flow path on the open-to-atmosphere side of the valve V16, closes the flow path on the positive pressure source P12 side of valve V17, and then, starts rotation of the stirrer R (S101). Subsequently, the preparation control section 28 fills the space S1 with the diluent (S102).

Specifically, in S101, first, the valve V24 is opened, and then, the diluent is supplied into the space S1 through the hole H23. At this time, the diluent moves into the receptacle 210 through the flow path 241. Then, when a predetermined time period has elapsed after the liquid level reached the height of the pin 212, the valve V24 is closed and the supply of the diluent is stopped. Accordingly, the liquid level enters the state shown in FIG. 16B. Then, the valves V13 and V15 are opened, and a negative pressure is applied by the negative pressure source P11 into the space S2 through the hole H31, whereby the diluent in the space S1 and the receptacle 210 is aspirated toward the space S2 side through the filter F4. When the space S2 is filled with the diluent, the valves V13 and V15 are closed. Accordingly, as shown in FIG. 16C, the space S2 is filled with the diluent.

Next, the preparation control section 28 causes the specimen pipette section 11 to aspirate the sample from the sample receptacle 12a of the first dispersion section 12, by the aspiration amount determined in S13 in FIG. 14 (S103). Subsequently, the preparation control section 28 causes the pipette 11a to be inserted into the receptacle 210 from above the top plate 120 through the hole 120b and the insertion hole 211, and causes the sample aspirated in S103 to be discharged into the receptacle 210 (S104). Accordingly, the liquid level enters the state shown in FIG. 16D.

Next, the preparation control section 28 causes a negative pressure to be applied into the space S2, to start aspiration of the liquid (diluent and sample) in the space 51 and the receptacle 210 (S105). Specifically, the valves V13 and V15 are opened, a negative pressure is applied into the space S2 by the negative pressure source P11, whereby the liquid in the space S1 and the receptacle 210 is aspirated toward the space S2 side through the filter F4. Subsequently, as shown in FIG. 16E, when the liquid level in the receptacle 210 has reached the height of the pin 213 (S106: YES), then, after a predetermined time period has elapsed, the preparation control section 28 closes the valves V13 and V 15, to stop aspiration under the negative pressure (S107). Accordingly, the liquid level enters the state shown in FIG. 16F.

Next, the preparation control section 28 causes a counter pressure (positive pressure) to be applied into the space S2, to push cells clogged in holes of the filter F4 and cells attached to the face on the space S1 side of the filter F4, into the space S1 (S108). Specifically, the flow path on the positive pressure source P12 side of the valve V17 is opened, and a positive pressure is applied into the space S2 by the positive pressure source P12, whereby the above cells are pushed into the space S1. When the pushing under the counter pressure ends, the flow path on the positive pressure source P12 side of the valve V17 is closed.

Next, when the process from S105 to S108 is in the first round or the second round (S109: NO), the preparation control section 28 causes the diluent to be supplied to the receptacle 210 (S110). Specifically, the valve V24 is opened, and the diluent is supplied into the space Si through the hole H23. At this time, the diluent moves to the receptacle 210 through the flow path 241. Then, when a predetermined time period has elapsed after the liquid level reached the height of the pin 212, the valve V24 is closed and the supply of the diluent is stopped. Accordingly, the liquid level enters the state shown in FIG. 16D. Then, the process is returned to S105, and the process from S105 to S108 is repeated three times in total.

In this manner, the preservative liquid whose major component is methanol and which is included in the sample is substituted with the diluent, and contaminants and cells other than analysis target cells contained in the sample are separated. In addition, in the space S1, a concentrate in which analysis target cells are concentrated is generated.

Next, when the process from S105 to S108 has been performed three times (S109: YES), the preparation control section 28 opens the space S2 to the atmosphere (S111). Specifically, from the state of the liquid level shown in FIG. 16F, the flow path on the open-to-atmosphere side of the valve V17 and the valve V16 are opened, and accordingly the inside of the space S2 is made to have the atmospheric pressure, whereby the liquid in the space S1 moves toward the receptacle 210 side. Subsequently, when the liquid level in the receptacle 210 has reached the height of the pin 213 (S112: YES), the preparation control section 28 closes the flow path on the open-to-atmosphere side of the valve V17 and the valve V16, stops allowing the space S2 to be open to the atmosphere (S113), and stops rotation of the stirrer R (S114).

Accordingly, the concentrate of analysis target cells generated in the space S1 is moved from the space S1 toward the receptacle 210, and the liquid level enters the state shown in FIG. 16G. As a result, in a lower portion of the receptacle 210, the concentrate of analysis target cells is reserved. At this time, the concentration of the concentrate is highest at the lower portion of the receptacle 210, and decreases from the lower portion of the receptacle 210 toward the space S1.

Next, as shown in FIG. 16H, the preparation control section 28 causes the pipette 11a to be inserted from above the top plate 120 through the hole 120b and the insertion hole 211 into the deepest portion of the receptacle 210. Then, the preparation control section 28 causes the pipette 11a to aspirate the concentrate reserved at the deepest portion of the receptacle 210 (S115). Accordingly, the liquid level enters the state shown in FIG. 16I. Then, the separation/substitution process ends, and based on the concentrate aspirated by the pipette 11a in S115, the process after S15 in FIG. 14 is performed.

It should be noted that in the state shown in FIG. 16H, the space S2 is not open to the atmosphere. Thus, there are cases where, when the aspiration by the pipette 11a ends, very small amounts of the concentrate remain in the space S1 and the flow path 241, as shown in FIG. 16I.

As described above, the present embodiment includes a configuration that moves the liquid in the space S1 through the filter F4 into the space S2 by use of a negative pressure. Therefore, the liquid present in the space S1 can be completely aspirated to the space S2 side, and the amount of cells other than analysis target cells remaining in the space S1 can be reduced as much as possible. In addition, in this separation/substitution section 14, the process of concentrating analysis target cells can be performed by use of a negative pressure and a positive pressure without moving the filter F4, and thus, the concentrating process can be performed quickly. Accordingly, it is possible to increase efficiency in generating a concentrate in which analysis target cells are concentrated. In addition, a greater amount of the concentrate can be collected, and thus, a greater amount of the concentrate can be subjected to the analysis. Therefore, accuracy of analysis of cells can be increased.

According to the present embodiment, before aspiration under a negative pressure is started (S105 in FIG. 15), the space S1 formed by the recess 230 and the space S2 formed by the recess 162 are connected to each other via the filter F4 in a liquid tight manner. Accordingly, the liquid and the sample in the space Si can be moved to the space S2 without leak by use of a negative pressure.

According to the present embodiment, in a state where the spaces S1 and S2 are filled with the diluent via the hole H23, aspiration under a negative pressure is performed. Accordingly, the liquid and the sample in the space S1 can be moved to the filter F4 side under a low negative pressure, and thus, analysis target cells can be prevented from passing through the filter F4.

According to the present embodiment, the flow path connected to the hole H32 formed in the recess 162 is opened to the atmosphere by the valves V16 and V17, whereby the space S2 is made to have the atmospheric pressure. Accordingly, the liquid including analysis target cells in the space S1 moves to the receptacle 210 through the hole H22.

According to the present embodiment, the stirrer R provided in the recess 230 is rotated along the side face (filtering face) on the recess 230 side of the filter F4. Thus, a flow of the sample rotating along the face of the filter F4 on the space Si side can be generated. Accordingly, analysis target cells attached to the filter F4 can be smoothly removed from the filter F4.

According to the present embodiment, the recess 230 has the inner side face 232 which is round, the stirrer R is rotated about the central axis A of the inner side face 232, and the reservoir 233 is formed in the inner side face 232 so as to be recessed in a direction away from the central axis A. Accordingly, during the separation/substitution process, analysis target cells contained in the sample in the space S1 gather in the reservoir 233 due to the rotation of the stirrer R. Therefore, a concentrate in which analysis target cells are concentrated can be efficiently taken out through the hole H22 formed in the reservoir 233.

According to the present embodiment, as shown in FIG. 10, the filter F4 is set in the cylindrical inner side face F31 of the filter member F such that the interval between the filter F4 and the face F1 is d22, and the diameter d12 of the inner side face F31 is greater than the diameter d11 of the protrusion R21 including the flange portion R21a of the stirrer R, and smaller than the outer diameter d13 of the face R2 of the stirrer R. Accordingly, as shown in FIG. 11D, even when the stirrer R has moved toward the filter member F side, the face R2 restrains the protrusion R21 from coming into contact with the filter F4, and thus, the filter F4 can be prevented from being damaged. In addition, since the protrusion R21 is prevented from coming into contact with the filter F4, the widths in the Y axis direction of the recess 230 and the stirrer R can be set such that the protrusion R21 is located close to the filter F4. Accordingly, analysis target cells attached to the filter F4 can be effectively removed.

According to the present embodiment, the filter F4 is provided in the filter member F, and the filter member F is inserted between the recess 230 and the recess 162 through the hole 120b shown in FIG. 3 and the insertion hole 221 of the receptacle 220 shown in FIG. 5A. At this time, the filter F4 is located at a position (Y axis negative direction side) facing the opening 231 of the recess 230. Accordingly, the filter member F being a consumable article can be easily exchanged via the hole 120b and the insertion hole 221.

According to the present embodiment, the piston 160 forming the recess 162 is moved in the Y axis positive direction, whereby the filter member F inserted between the recess 230 and the recess 162 through the insertion hole 221 is pressed against the recess 230. Accordingly, the recess 230 and the recess 162 are connected together via the filter member F, and as shown in FIG. 11C, the space S1 which is closed can be easily generated in the recess 230.

According to the present embodiment, the filter member F is arranged such that the filtering face of the filter F4 is parallel to the XZ plane. When the filtering face of the filter F4 is arranged so as to be parallel to the vertical direction, compared with a case where the filtering face of the filter F4 is arranged so as to be parallel to the horizontal direction, the separation/substitution section 14 can be downsized in the horizontal direction. Accordingly, the measurement apparatus 2 can be downsized in the horizontal direction, and the installation area for the canceration information providing apparatus 1 including the measurement apparatus 2 can be reduced. In addition, analysis target cells attached to the filter F4 can be easily removed from the filter F4 due to gravity.

According to the present embodiment, the hole H22 is formed at a position below the recess 230. This facilitates analysis target cells having been removed from the filter F4 to gather in the vicinity of the hole H22 due to gravity. Therefore, analysis target cells can be efficiently collected via the hole H22.

According to the present embodiment, a mixed liquid (sample) composed of cells collected from a subject and a preservative liquid whose major component is methanol is discharged into the receptacle 210. The sample discharged into the receptacle 210 passes through the flow path 241 and flows into the recess 230 through the hole H22. In addition, by the valve V24 being opened, the diluent (substitution liquid) is flowed into the recess 230 through the hole H23. Accordingly, the preservative liquid can be substituted with the substitution liquid in the space S1. In addition, by closing the valve V24, it is possible to make the space S1 to be a space closed from the outside.

According to the present embodiment, as shown in FIG. 7A, with the filter F4 interposed between the holding member F100 and the holding member F200, the holding member F200 is fitted to the holding member F100, to integrate the holding members F100 and F200 together. Accordingly, the filter F4 is sandwiched by the holding members F100 and F200, to be mounted to the filter member F. At this time, the elastic bodies F140 and F240 are brought into close contact with the filter F4, and thus, the filter F4 is sandwiched by the holding members F100 and F200 firmly and in a highly liquid tight manner. Thus, according to the filter member F of the present embodiment, it is possible to mount the filter F4 to the filter member F inexpensively and through simple work, while increasing the mounting strength of the filter F4 to the filter member F. Therefore, it is possible to keep the production costs of the filter member F low.

According to the present embodiment, as shown in FIG. 8E, the stoppers F231 of the projecting pieces F230 are engaged with the engagement portions F131, respectively. Accordingly, the holding member F200 is fixed to the holding member F100, and thus, the filter F4 can be more firmly mounted to the filter member F.

According to the present embodiment, as shown in FIG. 7A, the filter F4 is provided with the thick portion F42 on the contact face with the elastic bodies F140 and F240. Accordingly, the thickness of the filter F4 is greater in the portion thereof sandwiched by the holding members F100 and F200, and thus, damage of the filter F4 can be prevented.

According to the present embodiment, as shown in FIGS. 6A and 6B, and FIGS. 8C and 8D, by the cutout F6 being formed, the filter member F has an asymmetric shape in the X axis direction (width direction). Accordingly, when the filter member F is mounted to the receptacle 220, the asymmetry of the filter member F is detected by the sensors 121 and 122. Therefore, it is possible to determine whether the filter member F has been appropriately mounted with its front and back sides correctly oriented.

According to the present embodiment, as shown in FIG. 7A to FIG. 8E, the holes F120 and F220 are each formed in a circular shape. Thus, when the holding members F100 and F200 are integrated together, the holes F120 and F220 form a cylindrical portion having the inner side faces F121 and F221 of a cylindrical shape. Accordingly, when the stirrer R is rotated, cells attached to the filter F4 can be easily and efficiently removed from the filter F4.

According to the present embodiment, as shown in FIGS. 8A and 8C, the rubber F51 is attached to the face F152 of the holding member F100. Accordingly, the liquid tightness between the filter F4 and the wall portion 222 of the receptacle 220 is improved.

According to the present embodiment, as shown in FIG. 8C, the rubber F51 is attached so as to be distanced from the boundary (inner circumference of the face F151) of the hole F120. Accordingly, the drive of the stirrer R can be smoothly performed without being hindered by the rubber F51, while the liquid tightness between the filter F4 and the wall portion 222 of the receptacle 220 is improved.

According to the present embodiment, as shown in FIGS. 8B and 8D, the rubber F52 is attached to the face F210 of the holding member F200. Accordingly, the liquid tightness between the filter F4 and the face 164 of the piston 160 is improved.

According to the present embodiment, the upper end portion F102 is formed in an upper portion of the holding member F100. In addition, it is configured such that, when the filter member F is mounted to the receptacle 220, the upper end portion F102 protrudes above the hole 120b of the top plate 120, together with an upper portion of the filter member F. Therefore, when the filter F4 is to be taken out from the receptacle 220, if the upper end portion F102 is gripped, the upper end portion F102 abuts against fingers, and accordingly, the holding member F100 can be easily caught by the fingers. Thus, the filter member F can be easily taken out.

An embodiment of the present invention has been described. However, the present invention is not limited to the above embodiment, and various modifications can be made to the above embodiment of the present invention.

For example, in the above embodiment, epidermal cells of the uterine cervix are the analysis target. However, cells of the oral cavity, other epidermal cells such as of the bladder or the pharynx, and further, epidermal cells of an organ may be the analysis target, and canceration of these cells may be determined.

In the above embodiment, as shown in FIG. 11D, the face R2 of the stirrer R restrains the protrusion R21 from coming into contact with the filter F4. However, the present invention is not limited thereto. It may be configured such that: the diameter of the barrel portion R1 is the same as the diameter d11 of the protrusion R21; and a plurality of projections radially projecting relative to the central axis A are provided between the protrusion R21 and the barrel portion R1. In this case, these projections restrain the protrusion R21 from coming into contact with the filter F4.

In the above embodiment, the reservoir 233 is formed in a lower portion of the inner side face 232 of the recess 230. Instead, the reservoir 233 may not be formed in the inner side face 232, and the hole H22 may be provided in a lower portion of the inner side face 232. Also in this case, the rotation of the stirrer R causes analysis target cells contained in the sample in the space S1 to gather in the vicinity of the hole H22 due to gravity. However, analysis target cells can be more effectively collected when the reservoir 233 is provided as in the above embodiment.

In the above embodiment, the measurement apparatus 2 performs measurement of analysis target cells and the data processing apparatus 3 performs analysis based on measurement data. However, the present invention is not limited thereto. These two apparatuses may be integrated together, and measurement and analysis of analysis target cells may be performed together.

In the above embodiment, as shown in FIG. 13, the preparation control section 28, the secondary detection section 13, the signal processing section 27, and the preparation device section 29 perform preparation of a measurement sample, and the measurement control section 25, the primary detection section 22, and the signal processing section 24 perform measurement of the measurement sample obtained through the preparation. However, the present invention is not limited thereto. The above mechanism for performing preparation of the measurement sample and the above mechanism for performing the measurement may be realized by different devices.

In the above embodiment, the projecting pieces F230 are provided in the holding member F200, and the engagement portions F131 to be engaged with the stoppers F231 of the projecting pieces F230 are provided in the holding member F100. However, the present invention is not limited thereto. Projecting pieces may be provided in the holding member F100, and engagement portions to be engaged with stoppers of the projecting pieces provided in the holding member F100 may be provided in the holding member F200.

Figure 17E:
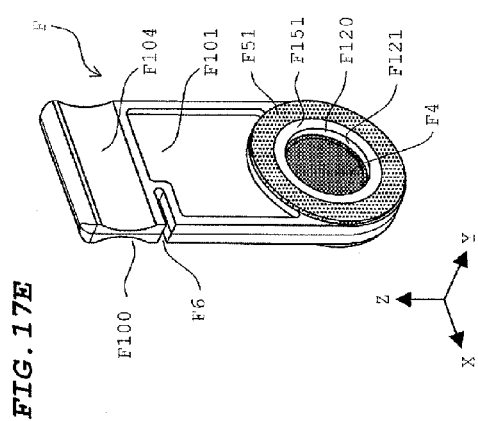
FIGS. 17A to 17F show configurations of filter members according to modifications.
Figure 17F:
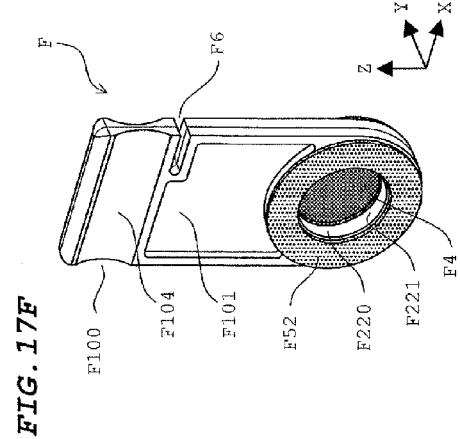

In the above embodiment, by the cutout F6 being formed, the filter member F has an asymmetric shape in the X axis direction (width direction). However, the present invention is not limited thereto. The filter member F may have an asymmetric shape in the Y axis direction (thickness direction). For example, as shown in FIGS. 17A and 17B, it may be configured such that, in the filter member F shown in FIGS. 8C and 8D, the cutout F6 is not formed and a flange portion F7 is formed on the face F101 on the Y axis positive direction side of the filter member F. In this case, instead of the sensors 121 and 122, a limit-type sensor is provided near the top plate 120. Accordingly, by means of the limit-type sensor, it is possible to determine whether the filter member F has been appropriately mounted with its front and back sides correctly oriented.

In the above embodiment, the face F101 recessed relative to the face therearound is formed in the filter member F, whereby the upper end portion F102 whose thickness is greater than that of the portion on the inner side in the longitudinal direction is provided in an upper portion of the filter member F. However, the configuration that allows the filter member F to be easily taken out is not limited thereto.

Figure 17C:
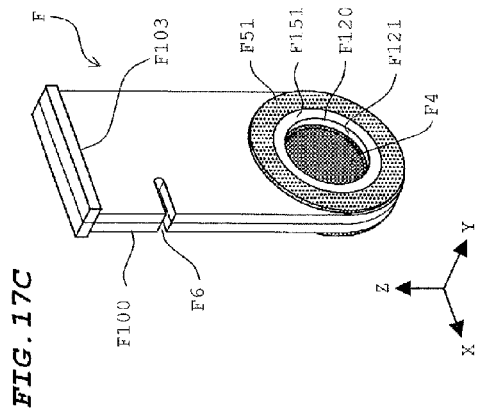
Figure 17D:
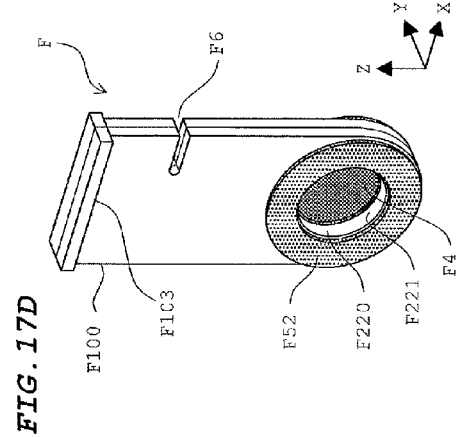
Figure 17A:
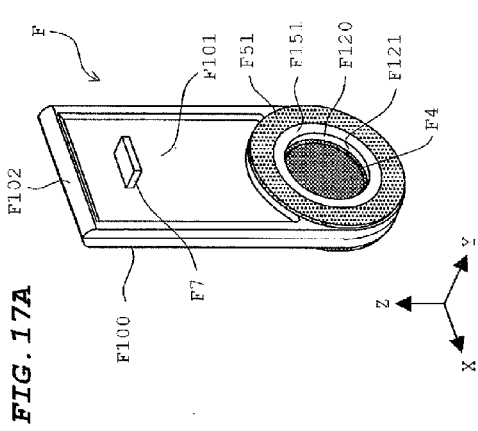
Figure 17B:
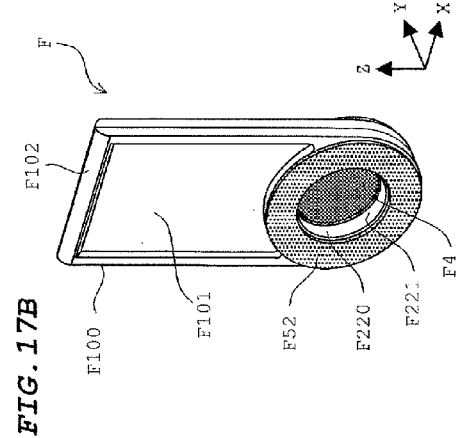

For example, as shown in FIGS. 17C and 17D, a ridge portion F103 protruding in the Y axis positive and negative directions may be formed at the upper end of the holding member F100. Alternatively, as shown in FIGS. 17E and 17F, a deformed portion F104 having a concaved shape near the center thereof in the Z axis direction may be formed in an upper portion of the holding member F100. As in the cases of the upper end portion F102, the ridge portion F103, and the deformed portion F104, the arrangement position of the structure that can be easily caught by fingers may be another position as long as the structure is exposed to the outside when the filter member F has been mounted to the receptacle 220.

In the above embodiment, a bar code, an RFID, or the like for identifying an individual filter member F may be affixed to an upper portion of the filter member F. This makes it easy to perform quality control of the filter member F, and thus, it is possible to appropriately perform exchange or the like of the filter member F.

Figure 18A:
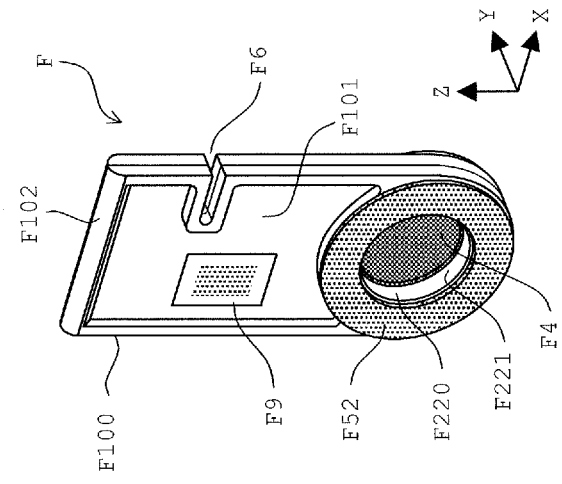
FIGS. 18A and 18B show configurations of filter members according to modifications.

FIG. 18A shows the filter member F to which a bar code label F8 is affixed. The bar code label F8 has a bar code printed thereon in which information (for example, expiration date) regarding this filter member F is recorded. When this filter member F is used, a bar code reader connected to the data processing apparatus 3 is used to read the bar code of the bar code label F8, and then, the filter member F is mounted in the receptacle 220. Accordingly, in the data processing apparatus 3, the filter member F can be individually recognized and the expiration date of the filter member F can be managed.

Figure 18B:
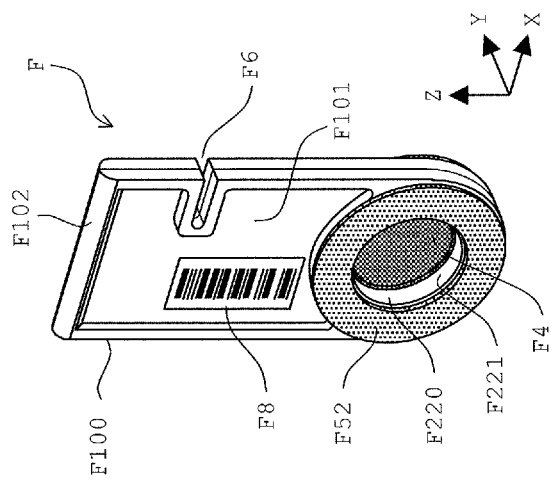

FIG. 18B shows the filter member F to which a RFID tag F9 is affixed. In the RFID tag F9, information (for example, expiration date) regarding this filter member F is recorded. In this configuration example, when the filter member F is mounted to the receptacle 220, the RFID tag F9 is automatically read by an antenna provided near the receptacle 220. Accordingly, in the data processing apparatus 3, the filter member F can be individually recognized and the expiration date of the filter member F can be managed.

In the above embodiment, based on outputs from the sensors 121 and 122, it is possible to detect whether the filter member F is correctly set. However, this detection result may be displayed on the display section 32 of the data processing apparatus 3. For example, when the set state of the filter member F is not appropriate, information indicating this may be displayed on the display section 32.

Figure 19B:
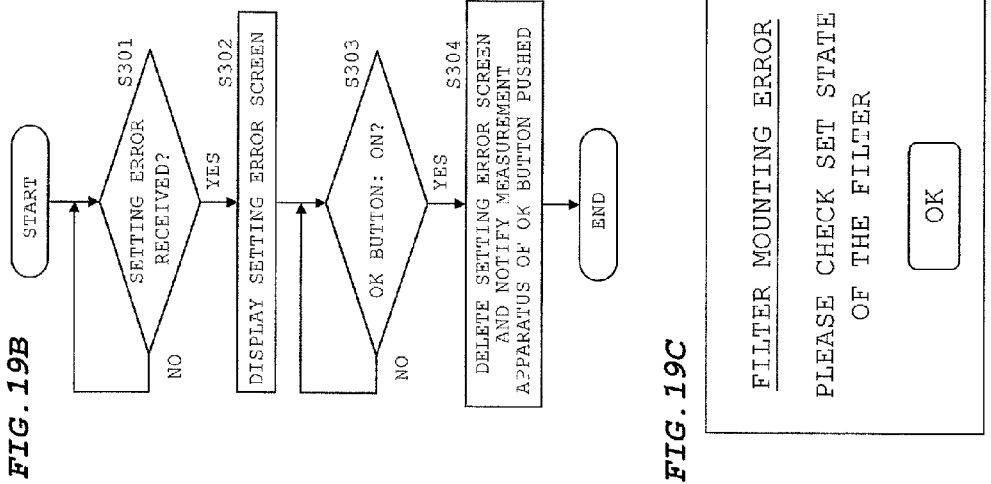
FIGS. 19A to 19C show examples of processes and a display when a filter member according to a modification is set in an erroneous manner.
Figure 19C:
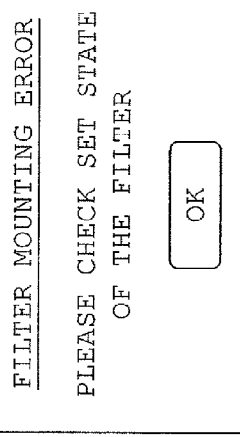
Figure 19A:
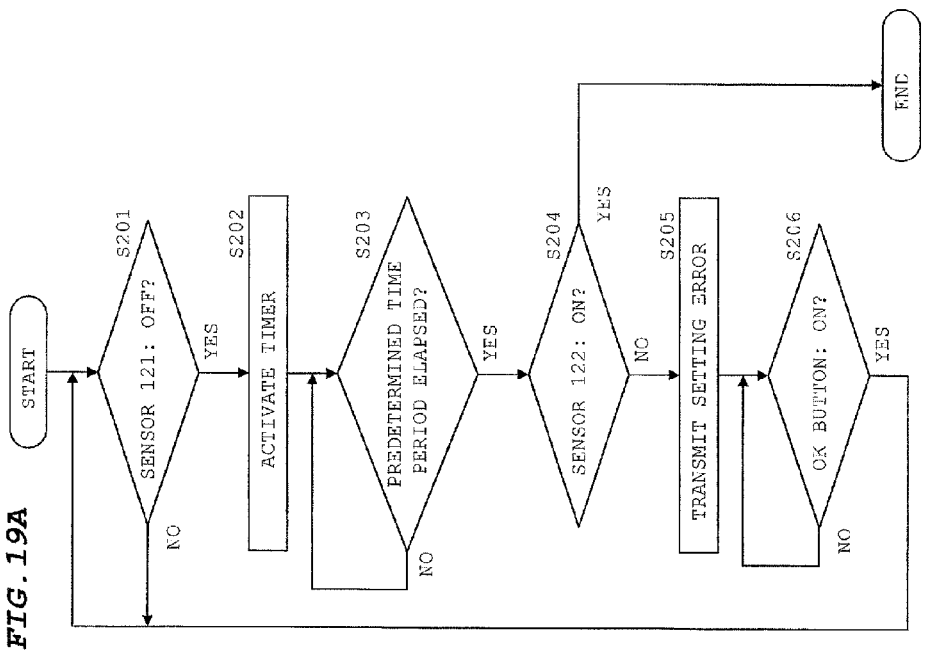

FIG. 19A is a flow chart showing a process example performed in the measurement apparatus 2 when the set state of the filter member F is to be determined. FIG. 19B is a flow chart showing a process example performed in the data processing apparatus 3 when the set state of the filter member F is to be determined. FIG. 19C shows a display example when the set state of the filter member F is not appropriate. The process shown in FIG. 19A is performed by the preparation control section 28 of the measurement apparatus 2.

With reference to FIG. 19A, first, based on signals supplied from the sensor section 291, the preparation control section 28 determines whether the light receiver of the sensor 121 has stopped receiving light (S201). When the light receiver of the sensor 121 has stopped receiving light (S201: YES), the preparation control section 28 activates a timer (S202), and determines whether a predetermined time period has elapsed from the timing when the light receiver of the sensor 121 stopped receiving light (S203). When the predetermined time period has elapsed from the activation of the timer (S203: YES), the preparation control section 28 determines whether the light receiver of the sensor 122 has received light at that timing (S204).

When the light receiver of the sensor 122 has received light (S204: YES), the preparation control section 28 determines that the filter member F has been correctly set, and ends the process. On the other hand, when the light receiver of the sensor 122 has not received light (S204: NO), the preparation control section 28 determines that the set state of the filter member F is not appropriate, and transmits setting error data indicating this to the data processing apparatus 3.

With reference to FIG. 19B, upon receiving the setting error data (S301: YES), the data processing apparatus 3 causes the display section 32 to display a setting error screen shown in FIG. 19C (S302). By viewing this screen, the user can know that the set state of the filter member F is not appropriate. The user sets the filter member F again with the orientation of the filter member F changed as appropriate, and then, pushes an OK button on the screen by operating the input section 31. When the OK button is pushed (S303: YES), the data processing apparatus 3 deletes the setting error screen, and transmits, to the measurement apparatus 2, data indicating that the OK button has been pushed (S304).

With reference back to FIG. 19A, upon receiving the data indicating that the OK button has been pushed (S206: YES), the preparation control section 28 of the measurement apparatus 2 returns the process to S201, and performs the process from S201 and thereafter, again. Then, when the determination in step S204 becomes YES, the preparation control section 28 determines that the filter member F has been correctly set, and ends the process. It should be noted that the operation explained with reference to FIGS. 11A to 11D is performed after the determination in S204 in FIG. 19A has become YES.

According to this configuration example, it is possible to notify the user that the filter member F is not appropriately set, and thus, it is possible to prevent the filter member F from being set in an erroneous manner. In addition, by viewing the screen shown in FIG. 19C, the user can smoothly take measures thereafter.

In addition to the above, various modifications can be made as appropriate without departing from the scope of the technology idea defined by the claims.

What is claimed is:

1. A sample preparation device comprising:
a filter member including a filter which separates cells being an analysis target from other component in a sample, the sample comprising the cells which are the analysis target, the component other than the analysis target and a first liquid, wherein the filter member comprises an indented cylindrical portion forming a surrounding cylindrical inner side face, and the filter is disposed within the indented cylindrical portion displaced at a defined distance away from an top surface of the filter member;
a first receptacle and a second receptacle connected to each other via the filter member which is disposed between the first receptacle and the second receptacle, a communication hole being formed within a recess cavity of the first receptacle and allowing the sample to go into and out of the first receptacle, wherein the recess cavity of the first receptacle fully contains a rotating member having a rotating surface which comprises an inner circular portion of a first diameter and a restraining portion concentrically formed around the inner circular portion with a second diameter wherein the second diameter is larger than the first diameter, wherein the inner circular portion is formed on top of the restraining portion such that when the inner circular portion is inserted into the indented cylindrical portion, the restraining portion restrains the inner circular portion from coming into contact with the filter, wherein a protrusion portion is formed on the inner circular portion, and the protrusion portion when rotated with the rotating member which is contained within the recess cavity, facilitates removal of the cells in the sample collected on a surface of the filter facing the recess cavity;

a third receptacle for holding the sample therein;

a flow path which allows the third receptacle to be communicated with the communication hole;

a negative pressure section which applies a negative pressure into the second receptacle, thereby to move the sample in the third receptacle toward the filter via the flow path and the first receptacle, and thereby to move the component other than the analysis target into the second receptacle via the filter; and a positive pressure section which applies a positive pressure from the second receptacle side to the filter to which the cells are attached; and a liquid supply part for supplying a second liquid which is different from the first liquid to the first receptacle and the second receptacle, wherein the negative pressure section operates in a state where both the first receptacle and the second receptacle are filled with the second liquid by the liquid supply part, to move the component other than the analysis target and the first liquid from the first receptacle to the second receptacle via the filter.

2. The sample preparation device according to claim 1, wherein the first receptacle and the second receptacle are connected to each other via the filter in a liquid tight manner, and the negative pressure section moves the sample in the first receptacle to the filter side.

3. The sample preparation device according to claim 1, wherein the second receptacle includes a vent hole for opening the second receptacle to the atmosphere, the sample preparation device further includes a valve for opening and closing the vent hole, and by the vent hole being opened by the valve, the liquid including cells being the analysis target in the first receptacle is moved into the third receptacle through the communication hole.

4. The sample preparation device according to claim 1, further comprising:

the rotating member rotates along a filtering face of the filter.

5. The sample preparation device according to claim 4, wherein the first receptacle includes a reservoir for reserving cells being the analysis target, the communication hole is provided in the reservoir, and the reservoir is located at a position where cells being the analysis target move into the reservoir due to a flow of the sample generated by rotation of the rotating member.

6. The sample preparation device according to claim 5, wherein the first receptacle has a round inner side face, the rotating member rotates about a central axis of the round inner side face, and the reservoir is formed in the round inner side face so as to be recessed in a direction away from the central axis.

7. The sample preparation device according to claim 1, wherein the cylindrical portion of the filter member includes a first opening and a second opening, the filter member includes, in an outer periphery of the first opening, an abutment portion which abuts against the restraining portion, the filter member is provided with an elastic body in an outer periphery of the abutment portion, and the abutment portion is not provided with an elastic body.

8. The sample preparation device according to claim 7, wherein an elastic body is provided in an outer periphery of the second opening.

9. The sample preparation device according to claim 1, wherein the filter is located nearer to one side in a thickness direction in the cylindrical portion.

10. The sample preparation device according to claim 1, comprising an insertion hole for inserting the filter member including the filter between the first receptacle and the second receptacle.

11. The sample preparation device according to claim 10, comprising a pressing mechanism which moves the second receptacle to the first receptacle side such that the filter member inserted from the insertion hole between the first receptacle and the second receptacle is pressed against the first receptacle.

12. The sample preparation device according to claim 10, further comprising:

a light source, and a light receiver which receives light from the light source, wherein the filter member includes a cutout in either one of end portions in a width direction thereof, and when the filter member has been inserted in a predetermined posture into the insertion hole, light from the light source reaches the light receiver through the cutout, and when the filter member has been inserted in a posture different from the predetermined posture into the insertion hole, light from the light source is blocked by the filter member and does not reach the light receiver.

13. The sample preparation device according to claim 12, further comprising:

a display section which displays, when the filter member has been inserted in a posture different from the predetermined posture into the insertion hole, that the filter member has been inserted in a posture different from the predetermined posture.

14. The sample preparation device according to claim 10, wherein the filter member further includes a deformed portion near an end portion thereof distanced in a longitudinal direction from a position where the filter is located, the deformed portion having a thickness greater than that on an inner side thereof in the longitudinal direction, and the filter member has a length that causes the deformed portion to protrude above the insertion hole when the filter member has been inserted in the insertion hole.

15. The sample preparation device according to claim 1, wherein the filter is located such that a filtering face of the filter is substantially parallel to a vertical direction.

16. The sample preparation device according to claim 15, wherein the communication hole is located at a position below the first receptacle.

17. The sample preparation device according to claim 1, wherein the third receptacle allows a pipette to be inserted thereinto, and receives the sample discharged from the pipette.

18. The sample preparation device according to claim 1, wherein a sample being a mixed liquid composed of a biological sample and a preservative liquid is flowed through the communication hole into the first receptacle, the first receptacle includes the liquid supply part for flowing a substitution liquid into the first receptacle, and the sample preparation device further includes a valve for opening and closing the liquid supply part.

19. The sample preparation device according to claim 1, wherein the sample includes a biological sample collected from a uterine cervix, and cells being the analysis target are epidermal cells of the uterine cervix.

20. The sample preparation device according to claim 1, wherein the filter member being asymmetric either in a width direction or in a thickness direction thereof.

21. The sample preparation device according to claim 20, wherein the filter member has a left-right asymmetric shape by including a cutout in either one of end portions in the width direction.

22. The sample preparation device according to claim 1, wherein the filter member further includes a deformed portion near an end portion thereof distanced in a longitudinal direction from a position where the filter is located, the deformed portion having a thickness greater than that on an inner side thereof in the longitudinal direction.

23. The sample preparation device according to claim 1, wherein the filter member includes an identification body in which information regarding the filter member is recorded.

24. The sample preparation device according to claim 23, wherein the information regarding the filter member includes information regarding an expiration date of the filter member.

\* \* \* \* \*